US010934578B2

(12) United States Patent
Hughes et al.

(10) Patent No.: US 10,934,578 B2
(45) Date of Patent: Mar. 2, 2021

(54) METHOD OF ANALYSING DNA SEQUENCES

(71) Applicant: OXFORD UNIVERSITY INNOVATION LIMITED, Oxford (GB)

(72) Inventors: James R. Hughes, Headington (GB); James Davies, Headington (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/769,677

(22) PCT Filed: Oct. 24, 2016

(86) PCT No.: PCT/GB2016/053314
§ 371 (c)(1),
(2) Date: Apr. 19, 2018

(87) PCT Pub. No.: WO2017/068379
PCT Pub. Date: Apr. 27, 2017

(65) Prior Publication Data
US 2018/0312910 A1  Nov. 1, 2018

(30) Foreign Application Priority Data
Oct. 23, 2015 (GB) ..................... 1518843

(51) Int. Cl.
*C12Q 1/6827* (2018.01)
(52) U.S. Cl.
CPC ..... *C12Q 1/6827* (2013.01); *C12Q 2600/156* (2013.01)
(58) Field of Classification Search
CPC ................. C12Q 1/6827; C12Q 2600/156
See application file for complete search history.

(56) References Cited

U.S. PATENT DOCUMENTS

| | | | |
|---|---|---|---|
| 5,731,153 | A | 3/1998 | Lucas et al. |
| 2010/0081141 | A1 | 4/2010 | Chen et al. |
| 2013/0096009 | A1 | 4/2013 | Dekker et al. |
| 2013/0183672 | A1 | 7/2013 | de Laat et al. |

FOREIGN PATENT DOCUMENTS

| | | |
|---|---|---|
| GB | 2 517 936 B | 3/2015 |
| WO | 2009/099602 A1 | 8/2009 |
| WO | 2012/061600 A1 | 5/2012 |
| WO | 2012/108864 A1 | 8/2012 |
| WO | 2012/159025 A2 | 11/2012 |
| WO | 2014/168575 A1 | 10/2014 |
| WO | 2015/033134 A1 | 3/2015 |
| WO | 2015/123588 A1 | 8/2015 |
| WO | 2016/089920 A1 | 6/2016 |

OTHER PUBLICATIONS

Anguita, E., et al., "Deletion of the Mouse Alpha-Globin Regulatory Element (HS -26) Has an Unexpectedly Mild Phenotype", Blood, vol. 100(10), pp. 3450-3456, (2002).

Ay, F., et al., "Identifying Multi-Locus Chromatin Contacts in Human Cells Using Tethered Multiple 3C", BMC Genomics, vol. 16(1), p. 121, Feb. 25, 2015, doi:10.1186/512864-015-1236-7.
Bau, D., et al., "The Three-Dimensional Folding of the Alpha-Globin Gene Domain Reveals Formation of Chromatin Globules", Nat. Struct. Mol. Biol., vol. 18, pp. 107-114, (2011).
Bernet, A., et al., "Targeted Inactivation of the Major Positive Regulatory Element (HS-40) of the Human Alpha-Globin Gene Locus", Blood, vol. 86, pp. 1202-1211, (1995).
Buenrostro, J.D., et al., "Transposition of Native Chromatin for Fast and Sensitive Epigenomic Profiling of Open Chromatin, DNA-Binding Proteins and Nucleosome Position", Nature Methods, vol. 10(12), pp. 1213-1218, Oct. 6, 2013.
Davies, J., et al., "Multiplexed Analysis of Chromosome Conformation at Vastly Improved Sensitivity", Nature Methods, vol. 13(1), pp. 74-80, Nov. 23, 2015.
Dekker, J., et al., "Capturing Chromosome Conformation", Science, vol. 295(5558), pp. 1306-1311, Feb. 15, 2002, doi:10.1126/science.1067799. (Abstract only).
de Laat, W., et al., "Topology of Mammalian Developmental Enhancers and their Regulatory Landscapes", Nature, vol. 502(7472), pp. 499-506, Oct. 24, 2013, doi:10.1038/nature12753. (Abstract only).
de Wit, E., et al., "A Decade of 3C Technologies: Insights into Nuclear Organization", Genes & Dev., vol. 26, pp. 11-24, (2012).
Duan, Z., et al., "A Genome-Wide 3C-Method for Characterizing the Three-Dimensional Architectures of Genomes", Methods, vol. 58(3), pp. 277-288, Nov. 1, 2012, doi:10.1016/j.ymeth.2012.06.018.
Hesselberth, J.R., et al., "Global Mapping of Protein-DNA Interactions In Vivo by Digital Genomic Footprinting", Nat. Methods, vol. 6(4), pp. 283-289, (2009).
Hughes, J.R., et al., "Analysis of Hundreds of Cis-Regulatory Landscapes at High Resolution in a Single, High-Throughput Experiment", Nature Genetics, vol. 46(2), pp. 205-212, Jan. 12, 2014, doi:10.1038/ng.2871.
Hughes, J.R., et al., "Analysis of Hundreds of Cis-Regulatory Landscapes at High Resolution in a Single, High-Throughput Experiment", Nature Genetics, vol. 46(2), pp. 205-212, Jan. 12, 2014, Supplementary information.
Hughes, J.R. et al., "High-Resolution Analysis of Cis-Acting Regulatory Networks at the Alpha-Globin Locus", Philos. Trans. R Soc., Lond B Biol. Sci., vol. 368, 20120361 (2013).
Jager, R., et al., "Capture Hi-C Identifies the Chromatin Interactome of Colorectal Cancer Risk Loci", Nat. Commun., vol. 6, p. 6178, (2015), doi:10.1038/ncomms7178.

(Continued)

*Primary Examiner* — Robert H Havlin
(74) *Attorney, Agent, or Firm* — McDonnell Boehnen Hulbert & Berghoff LLP

(57) ABSTRACT

The present invention relates to a method of identifying nucleic acid regions within a nucleic acid sample which interact with one another. In particular, the method relates to a chromatin conformation capture (3C) method which may be used to analyse the interactions between enhancers, silencers, boundary elements and promoters at individual loci at high resolution.

16 Claims, 9 Drawing Sheets
Specification includes a Sequence Listing.

(56) References Cited

OTHER PUBLICATIONS

Kang, J.H., et al., "Genomic Organization, Tissue Distribution and Deletion Mutation of Human Pyridoxine 5'- Phosphate Oxidase", Eur. J. Biochem., vol. 271, pp. 2452-2461, (2004), doi:10.1111/j.1432-1033.2004.04175.x.

Kent, W.J., et al., "The Human Genome Browser at UCSC", Genome Res., vol. 12, pp. 996-1006, (2002).

Klein, F.A., et al., "FourCSeq: Analysis of 4C Sequencing Data", Bioinformatics, vol. 31(19), pp. 3085-3091, (2015), doi:10.1093/bioinformatics/btv335.

Kolovos,P., et al., "Targeted Chromatin Capture (T2C): A Novel High Resolution High Throughput Method to Detect Genomic Interactions and Regulatory Elements", Epigenetics & Chromatin, vol. 7(1), p. 10, Jun. 16, 2014, doi:10.1186/1756-8935-7-10.

Kowalczyk, M.S., et al., "Intragenic Enhancers Act as Alternative Promoters", Mol. Cell, vol. 45, pp. 447-458, (2012), doi:10.1016/j.molcel.2011.12.021.

Love, M.I. et al.,"Moderated Estimation of Fold Change and Dispersion for RNA-Seq Data with DESeq2", Genome . Biol., vol. 15, p. 550, (2014), doi:10.1186/s13059-014-0550-8.

Magoc, T., et al., "FLASH: Fast Length Adjustment of Short Reads to Improve Genome Assemblies", Bioinformatics, vol. 27, pp. 2957-2963, (2011), doi:10.1093/bioinformatics/btr507.

Maurano, M.T., et al., "Systematic Localization of Common Disease-Associated Variation in Regulatory DNA", Science, vol. 337(6099), pp. 1190-1195, Sep. 7, 2012, doi:10.1126/science.1222794.

Mikkelsen, T.S., et al., "Genome-Wide Maps of Chromatin State in Pluripotent and Lineage-Committed Cells", Nature, vol. 448(7153), pp. 553-560, Aug. 2, 2007, doi:10.1038/nature06008.

Noordermeer, D., et al., "Variegated Gene Expression Caused by Cell-Specific Long-Range DNA Interactions", Nat. Cell Biol., vol. 13(8), pp. 944-951, (2011), doi:10.1038/ncb2278.

Noordermeer, D., et al., "The Dynamic Architecture of Hox Gene Clusters", Science, vol. 334(6053), pp. 222-225, Oct. 14, 2011, doi:10.1126/science.1207194. (Abstract only).

Osborne, C.S., et al., "Active Genes Dynamically Colocalize to Shared Sites of Ongoing Transcription", Nat. Genet., vol. 36(10), pp. 1065-1071, Oct. 2004, doi:10.1038/ng1423.

Parker, S.C., et al., "Chromatin Stretch Enhancer States Drive Cell-Specific Gene Regulation and Harbor Human Disease Risk Variants", Proc. Natl. Acad. Sci. USA, vol. 110(44), pp. 17921-17926, Oct. 29, 2013.

Pasquali, L., et al., "Pancreatic Islet Enhancer Clusters Enriched in Type 2 Diabetes Risk-Associated Variants", Nat. Genet., vol. 46(2), pp. 136-143, Feb. 2014, doi:10.1038/ng.2870.

Prediger, E., "Understanding How Distal Regulatory Elements Control Gene Expression. Next Generation Chromosomal Conformational Capture (NG Capture-C) Technology", Decoded, pp. 1-8, Mar. 11, 2015.

Raney, B.J., et al., "Track Data Hubs Enable Visualization of User-Defined Genome-Wide Annotations on the UCSC Genome Browser", Bioinformatics, vol. 30(7), pp. 1003-1005, (2014), doi:10.1093/bioinformatics/btt637.

Rao, S.S., et al., "A Three-Dimensional Map of the Human Genome at Kilobase Resolution Reveals Principles of Chromatin Looping", Cell, vol. 159(7), pp. 1665-1680, Dec. 18, 2014, doi:10.1016/j.cell.2014.11.021.

Robertson, G., et al., "Genome-Wide Profiles of STAT1 DNA Association Using Chromatin Immunoprecipitation and Massively Parallel Sequencing", Nat. Methods, vol. 4(8), pp. 651-657, Aug. 2007, Epub Jun. 11, 2007. (Abstract only).

Sanyal, A., et al., "The Long-Range Interaction Landscape of Gene Promoters", Nature, vol. 489, pp. 109-113, Sep. 6, 2012, doi:10.1038/nature11279.

Schoenfelder, S., et al., "The Pluripotent Regulatory Circuitry Connecting Promoters to their Long-Range Interacting Elements", Genome Res., vol. 25, pp. 582-597, (2015).

Selvaraj, S., et al., "Whole-Genome Haplotype Reconstruction Using Proximity-Ligation and Shotgun Sequencing", Nature Biotechnology, vol. 31(12), pp. 1111-1118, Dec. 2013, doi:10.1038/nbt.2728.

Sexton, T., et al., "Sensitive Detection of Chromatin Co-associations Using Enhanced Chromosome Conformation Capture on Chip", Nature Protocols, vol. 7(7), pp. 1335-1350, Jun. 21, 2012, doi:10.1038/nprot.2012.071.

Simonis, M., et al., "Nuclear Organization of Active and Inactive Chromatin Domains Uncovered by Chromosome Conformation Capture-On-Chip (4C)", Nat. Genet., vol. 38(11), pp. 1348-1354, Nov. 2006, Epub Oct. 8, 2006. (Abstract only).

Takahashi, K., et al., "Induction of Pluripotent Stem Cells from Mouse Embryonic and Adult Fibroblast Cultures by Defined Factors", Cell, vol. 126, pp. 663-676, Aug. 25, 2006, doi:10.1016/j.cell.2006.07.024.

Thongjuea, S., et al., "r3Cseq: An R/Bioconductor Package for the Discovery of Long-Range Genomic Interactions from Chromosome Conformation Capture and Next-Generation Sequencing Data", Nucleic Acids Research, vol. 41 (13), e132, pp. 1-12, (2013), doi:10.1093/nar/gkt373.

Tolhuis, B., et al, "Looping and Interaction Between Hypersensitive Sites in the Active Beta-Globin Locus", Molecular Cell, vol. 10, pp. 1453-1465, Dec. 2002.

van de Werken, H.J., et al., "Robust 4C-Seq Data Analysis to Screen for Regulatory DNA Interactions", Nat. Methods, vol. 9(10), pp. 969-972, Oct. 2012, doi:10.1038/nmeth.2173, Epub Sep. 9, 2012.

Vernimmen, D., et al., "Long-Range Chromosomal Interactions Regulate the Timing of the Transition Between Poised and Active Gene Expression", The EMBO Journal, vol. 26, pp. 2041-2051, (2007).

Wang, Z., et al., "RNA-Seq: A Revolutionary Tool for Transcriptomics", Nat. Rev. Genet., vol. 10(1), pp. 57-63, Jan. 2009, doi:10.1038/nrg2484.

Zhang, J., et al., "ChIA-PET Analysis of Transcriptional Chromatin Interactions", Methods, vol. 58(3), pp. 289-299, Nov. 1, 2012, doi:10.1016/j.ymeth.2012.08.009.

"Trim Galore", Babraham Bioinformatics, pp. 1-5, [Retrieved from the Internet Jul. 26, 2018: <URL:http://www.bioinformatics.babraham.ac.uk/projects/trim_galore/>].

"CaptureC Codes as They Were at the Time of Publication", Telenius, [Retrieved from the Internet Jul. 26, 2018: <URL:https://github.com/telenius/captureC/releases>].

Davies, J., et al., "Next Generation Capture-C: A Highly Sensitive and Scalable Method for Multiplexed Definition of Chromatin Structure", Poster presented at the SAID Business School, Oxford, UK (Mar. 27, 2015).

Davies, J., "Next Generation Capture-C: A Highly Sensitive Technique for Determining Chromatin Interactions", PowerPoint presentation, pp. 1-24, given at the Medical Sciences Division, Oxford, UK (Jul. 9, 2015).

Davies, J., "Linking Promoters with their Regulatory Elements During Erythropoiesis", (PowerPoint presentation, 20 pages), given at the EMBO Nuclear Structure and Dynamics meeting, L'Isle sur la Sorgue, France (Oct. 5, 2013).

Hsieh, T-H.S., et al., "Mapping Nucleosome Resolution Chromosome Folding in Yeast by Micro-C", Cell, Jul. 2, 2015, vol. 162(1), pp. 108-119, doi:10.1016/j.cell.2015.05.048.

Hughes, J., "Identifying Distal Regulators Using Chromatin Profiles and Capture C", 18th Annual Conference on Hb Switching, California, USA (Jun. 7-11, 2012) (Abstract only).

Hughes, J.R., et al., "Linking Promoters with their Regulatory Elements During Erythropoiesis", EMBO Nuclear Structure and Dynamics meeting, L'Isle sur la Sorgue, France (Sep. 30, 2013) (Abstract only).

Nagano, T., et al., "Comparison of Hi-C Results Using In-Solution Versus In-Nucleus Ligation", Genome Biology, 2015, vol. 16(175), pp. 1-13, doi:10.1186/s13059-015-0753-7.

Schmitt, A.D., et al., "Genome-Wide Mapping and Analysis of Chromosome Architecture", Nature Reviews, Molecular Cell Biology, Sep. 1, 2016, vol. 17(12), pp. 743-755, doi:10.1038/nrm.2016.104.

(56) References Cited

OTHER PUBLICATIONS

International Preliminary Report on Patentability, from the International Bureau of WIPO, for International Application No. PCT/GB2016/053314, dated Apr. 24, 2018, pp. 1-13.

International Search Report and Written Opinion, from the International Searching Authority, for International Application No. PCT/GB2016/053314, dated Jan. 16, 2017, pp. 1-10.

U.K. Search Report, received from the U.K. Patent Office, for Great Britain Patent Application No. GB1518843.6, dated Sep. 14, 2016, pp. 1-33.

Takashi N. et al., Genome Biology, vol. 16, 2015, "Comparison of Hi-C Results Using In-Solution Versus In-Nucleus Ligation", pp. 1-13.

b.

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
gtgtcaccaa aaccagctca                                          20

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
cctggaatcc tttggctcaa g                                        21

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
gggcagctaa gatgcaagtc                                          20

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
tggagggcat ataagtgcta cttg                                     24

<210> SEQ ID NO 5

```
<211> LENGTH: 21
<212> TYPE: DNA
<213> ORGANISM: Artificial Sequence
<220> FEATURE:
<223> OTHER INFORMATION: PCR primer

<400> SEQUENCE: 5
tgcttttgtc ttccccagag a                                             21

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
tgcaggtcca agacacttct gattctgaca                                    30
```

METHOD OF ANALYSING DNA SEQUENCES

CROSS-REFERENCE

This application is a section 371 U.S. National phase of PCT/GB2016/053314, filed Oct. 24, 2016 which claims priority from GB 1518843.6, filed Oct. 23, 2015, which is incorporated by reference in its entirety.

FIELD OF THE INVENTION

The present invention relates to a method of identifying nucleic acid regions within a nucleic acid sample which interact with one another. In particular, the method relates to a chromatin conformation capture (3C) method which may be used to analyse the interactions between enhancers, silencers, boundary elements and promoters at individual loci at high resolution.

BACKGROUND OF THE INVENTION

Progress in our ability to annotate regulatory elements in the genome and determine their potential function has been driven by technological advances, such as RNA-seq [1], ChIP-seq [2, 3], DNase-seq [4] and ATAC-seq [5]. However, an outstanding challenge is to understand the mechanisms by which regulatory elements control specific gene promoters at a distance (10 s to 1000 s kb).

Using conventional Chromosome Conformation Capture (3C), it is possible to analyse in detail the interactions between enhancers, silencers, boundary elements and promoters at individual loci at high resolution [6-11].

Since the development of the original 3C method in 2002 [6], several new 3C-based techniques have emerged such as Capture-C, Hi-C, Capture Hi-C, in situ Hi-C, Circularized Chromosome Conformation Capture (4C), 4C-seq, ChIA-PET and Carbon Copy Chromosome Conformation Capture (5C). Each of these techniques has its particular strengths and weaknesses.

There is still a need for more chromosome conformation capture protocols with increased sensitivity and resolution, that are straightforward to perform, but which can generate data in a high throughput manner. Existing technologies are generally performed by specialist laboratories; such technologies are very difficult to set up and analyse in standard laboratories.

SUMMARY OF THE INVENTION

The sheer variety of techniques which are currently available creates a challenge when attempting to improve yet further on the sensitivity of the basic 3C technique. All 3C techniques require an enrichment step, the basis of which varies across most of the methods and it often unclear which will prove to be the most efficient and flexible approach. Furthermore, issues such as the choice of restriction endonucleases or fragmentation method, cross-linking stringency, primer design, library complexity and probe position can all have an effect on the efficacy of any one particular enrichment method.

The current inventors selected the Capture-C protocol as their basic starting point and they re-evaluated all of the steps of this protocol in an attempt to increase sensitivity and flexibility of the Capture-C enrichment approach, while maintaining its operational simplicity.

The original Capture-C protocol [12] used oligos synthesized on a microarray (Agilent SureSelect) with a minimum design of 40,000 oligos, irrespective of the number of desired viewpoints; the cost per sample was therefore very high for small designs. Laboratories more often want to analyse a much smaller subset of regions in several different samples. Furthermore, the sensitivity possible with this previous design did not readily allow for the analysis of very long-range cis-interactions or trans-interactions and did not provide quantitative estimates of megabase-scale chromosomal interactions. Importantly, although the method was high throughput at the level of which regions of the genome it could analyse simultaneously, it was still limited to one sample per assay.

A further adaptation of the original Capture-C method is the Capture-Hi-C method (as exemplified in WO2015/033134) which combines the Capture-C method with the Hi-C library production. The Capture-Hi-C method requires the superimposition of a biotin group during the ligation step of library production to capture (as illustrated in FIG. 1 of WO2015/033134). This step is inefficient and so can greatly decrease the complexity of the library; ultimately, it greatly limits the sensitivity of the approach. Loss of complexity in the library is directly related to the amount of information that can be extracted per cell of the original sample. Therefore methods which involve such losses are only readily usable in circumstances where very large numbers of cells are available.

The current inventors were looking to improve yet further on the original Capture-C method.

Analysis of the original Capture-C data showed that the sonication step allowed the identification of PCR duplicates in this assay, an effect that is problematic in most existing 3C methods. This allowed for the direct measurement of the efficiency of enrichment for ligation junction in the assay and made it possible to determine when all information had been extracted from a given library and where further sequencing would not yield any further information. By performing an experiment targeting a single gene promoter, it was surprisingly discovered that the captured DNA from this single region of interest made up less than 1% of the sequenced reads. This showed that great sequencing depth would be required in order to extract all of the information from the library with standard single capture. This would be completely impractical for smaller designs or repeated experiments, and it showed that simplifying the design itself would not readily increase the signal to noise ratio. It suggested that the signal to noise ratio was in fact inherent to the then current capture protocol.

The direct measurement of enrichment and PCR duplication not only gave an excellent measure by which to quantify improvements in sensitivity, it also highlighted how crucial a factor initial library complexity was. For this reason, methods such as "biotin fill in" (e.g. WO2015/033134) were excluded as they detrimentally affected library complexity.

This lead to the understanding that a step was needed that would result in the depletion of this inherent background, without affecting library complexity. Based on the observation that the number of capture probes in the design did not drastically decrease the amount of background that had to be sequenced, it was realised that the background was actually coming from non-specific carry-through from the beads and other physical media such as tubes used in the process.

Due to the complete control over PCR duplicates in the Capture-C protocol, it was realised that the library could be substantially over-amplified in the initial step of the library preparation part of the protocol, so that each informative junction would be represented multiple times prior to capture. It was further realised that, as junctions were now robustly represented and that the background was not intrinsic to the capture probes themselves, then the remaining background could substantially further mechanically-depleted by a second round of capture without loss of complexity.

The inventors have now found that the use of two sequential oligonucleotide capture steps applied to a 3C library (e.g. a PCR duplicated 3C library) prior to sequencing results in up to 3,000,000 fold enrichment compared to an uncaptured 3C library so that captured material now makes up approximately 50% (rather than 1%) of the sequenced material. This second capture step increases the number of PCR cycles and the number of PCR duplicates sequenced because the library complexity (i.e. the number of interactions available to capture) limits the number of unique interactions that could be sequenced. The greatly improved enrichment means that the depth of sequencing is no longer limiting. Using this new method, any PCR duplicates can be easily and efficiently excluded bioinformatically.

Furthermore, due to the huge increase in signal, independent 3C libraries (e.g. from different cell types or different stages of development) can now be captured and processed in a single tube making separately-indexed samples directly comparable. This greatly increases throughput and allows meaningful subtractive analysis of chromosome conformation in different cell types.

The method of the invention is also usable with smaller numbers of cells than were previously required. Additionally, it can also be used to identify allele-specific interaction profile in SNP-containing regions.

The inventors have called their invention "Next Generation" (NG) Capture-C. NG Capture-C is able to detect interactions present 1 in 5-10,000 cells, which is far exceeds the current reasonable limit of detection by fluorescence in-situ hybridisation (FISH) [31].

The investigation of gene regulation is not only limited by the number of genes or elements that can be interrogated, but also by the number of replicates, conditions, cell types and genetic variants that can be easily analysed. The huge increase in signal of NG Capture-C allows for the simultaneous capture of multiple samples in a single reaction, greatly increasing the throughput and economy of the assay. In practice, this allows complete networks of important genes, such as those encoding the Yamanaka pluripotency factors [32] (Myc, Sox2, Oct4, Klf4) to be analysed simultaneously in multiple cell types. The data are compatible with standard analytical tools and their reproducibility and comparability between active and inactive states of NG Capture-C provides a complementary approach to the statistical identification of regulatory elements. This complementary approach is capable of identifying all known regulatory elements at well characterised test loci, at levels of resolution previously not possible. Importantly, mindful of the current challenges in the analysis of GWAS and regulatory variants, the NG Capture-C method can been optimized to be effective at smaller cell numbers (approximately 100,000 cells) and to generate SNP-specific interaction profiles.

In one embodiment, the invention provides a method of identifying nucleic acid regions within a nucleic acid sample which interact with one another, the method comprising the steps:

A. fragmenting a 3C library which was produced from the nucleic acid sample to produce nucleic acid fragments;

B. optionally, adding sequencing adaptors to the ends of the nucleic acid fragments and/or amplifying the nucleic acid fragments;

C. contacting the nucleic acid fragments with a targeting nucleic acid which binds to a subgroup of the nucleic acid fragments, wherein the targeting nucleic acid is labelled with the first half of a binding pair;

D. isolating the subgroup of nucleic acid fragments which have been bound by the targeting nucleic acid using the second half of the binding pair;

E. amplifying the isolated subgroup of nucleic acid fragments;

F. repeating Steps C, D and E; and optionally

G. sequencing the amplified isolated subgroup of nucleic acid fragments.

Preferably, the targeting nucleic acid is a DNA oligonucleotide.

Preferably, the concentration of the targeting nucleic acid is 5 µM to 1 pM, more preferably 1 µM to 30 pM, even more preferably 300 nM to 30 pM, and most preferably 30 nM to 0.3 nM (e.g. about 2.9 nM).

Preferably, Step F is repeated 1, 2, 3, 4 or 5 times, preferably 1 or 2 times.

In a further embodiment, there is provided a method of identifying allele-specific interaction profiles in SNP-containing regions, the method comprising the method of the invention including sequencing the amplified isolated subgroup of nucleic acid fragments in order to identify allele-specific interaction profiles in SNP-containing regions.

In a yet further embodiment, there is provided a kit for identifying nucleic acid regions within a nucleic acid sample which interact with one another, the kit comprising buffers and reagents for performing the method of the invention.

In a yet further embodiment, there is provided a method of identifying one or more interacting nucleic acid regions that are indicative of a particular disease state or disorder, the method comprising:

a) carrying out a method as defined herein on a nucleic acid sample obtained from a subject with a particular disease state or disorder;

b) quantifying a frequency of interaction between a first nucleic acid region and a second nucleic acid region; and c) comparing the frequency of interaction in the nucleic acid sample from the subject with said disease state or disorder with the frequency of interaction in a control nucleic acid sample from a healthy subject, such that a difference in the frequency of interaction in the nucleic acid samples is indicative of a particular disease state or disorder.

Figure 1:
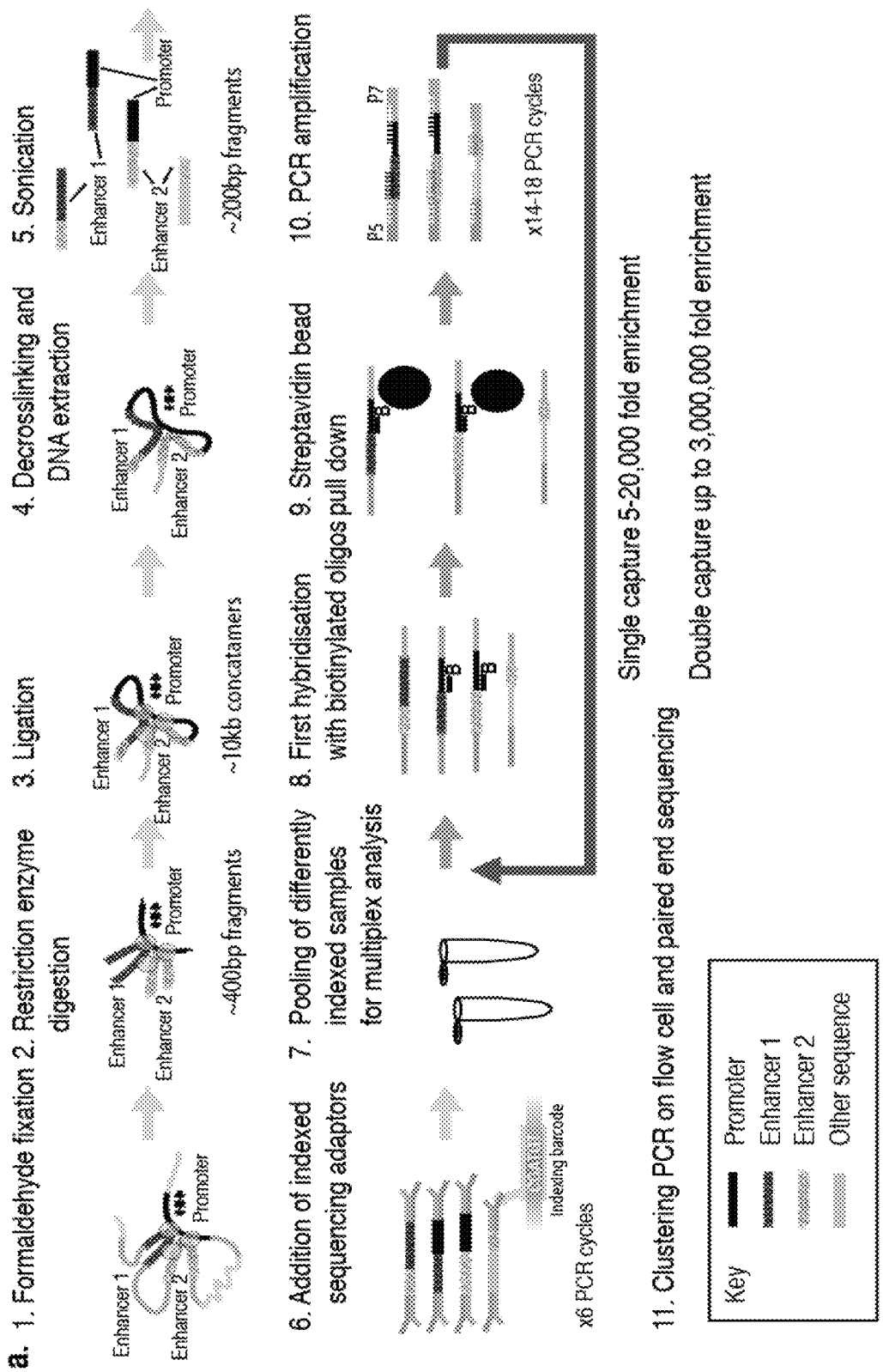
FIG. 1 illustrates an overview of an embodiment of the method of the invention.
Figure 1:
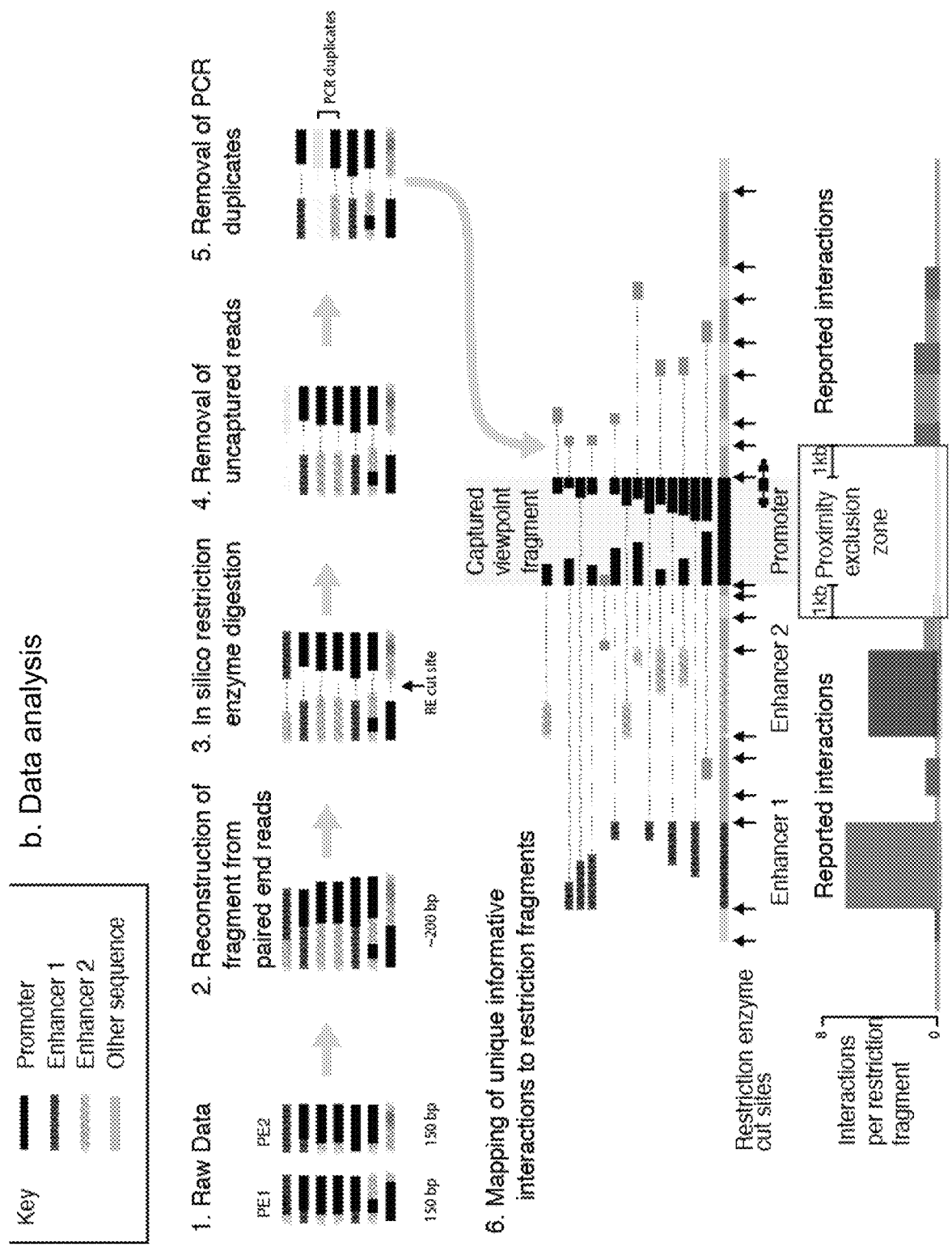

a. Experimental workflow. 3C libraries were made using a very similar method to the protocol for in situ Hi-C: namely, formaldehyde crosslinking of live cells (1); restriction enzyme digestion of chromatin (optimized for a four cutter restriction enzyme (e.g. Dpn II)) (2); ligation (3); de-crosslinking and DNA extraction (4). In order to prepare the 3C library for oligonucleotide capture the material is sonicated, which randomly generates ~200 bp fragments (5). Sequencing adaptors are then ligated and different indices are added by ligation-mediated PCR (6). Differently indexed samples can then be pooled (7) prior to hybridization with biotinylated oligonucleotides, which allows a single capture reaction to be performed on multiple samples. The captured sequences are then pulled down using streptavidin beads (9) and the material is PCR amplified off the beads using the P5&7 sequences in the sequencing adaptors (10). Steps 8-10 are then repeated. This results in very significant further enrichment: up to 3,000,000-fold over the baseline uncaptured 3C library. The material is then sequenced using either Illumina Miseq (150 bp, paired end) or Hiseq (100 bp, paired end). Note that the clustering on the flow cell uses the same PCR primers as all of the other PCR steps in the protocol and that 35 cycles are used for clustering compared to 34 cycles in the entire double capture protocol.

b. Data analysis. 1. The raw data are taken in FASTQ format. 2. Initially, the paired end reads are reconstructed into single sequences using the central area of overlap to align the sequences. This is possible for 95% of the reads because the material is sonicated into 200 bp fragments, which are then sequenced with 300 bp reads (150 bp paired end). 3. Next, each read is split in silico using the restriction enzyme recognition sequence. This ensures that the reported ligation junctions contain the correct restriction enzyme cut sequence. This splits the reads into its component restriction fragments and the read name is used to link sets of fragments from the same read. 4. Reads that do not contain a sequence that maps inside the captured viewpoint restriction fragment are discarded. 5. Reads that are not unique (based on the sonicated ends) are removed. 6. Interactions are only reported when the entire sequenced read is unique and when one component of a read pair maps completely within a captured fragment and the other maps outside all of the capture fragments and proximity exclusion regions in the experiment. The proximity exclusion zones are normally set at 1 kb on either side of the captured viewpoint fragment. This is done to prevent undigested material being reported as interacting and to prevent interactions being falsely reported from fragments that could be captured by two different oligonucleotides. The data are then filtered to remove regions with problematic mappability due to copy number differences and mis-mapped reads from the proximity exclusion region. Due to the depth of the sequence data obtained following double capture, unique interactions can be reported for each individual restriction fragment or half fragment, which is the highest possible resolution for such experiments; there is no requirement to integrate data by using a moving window.

Figure 2:
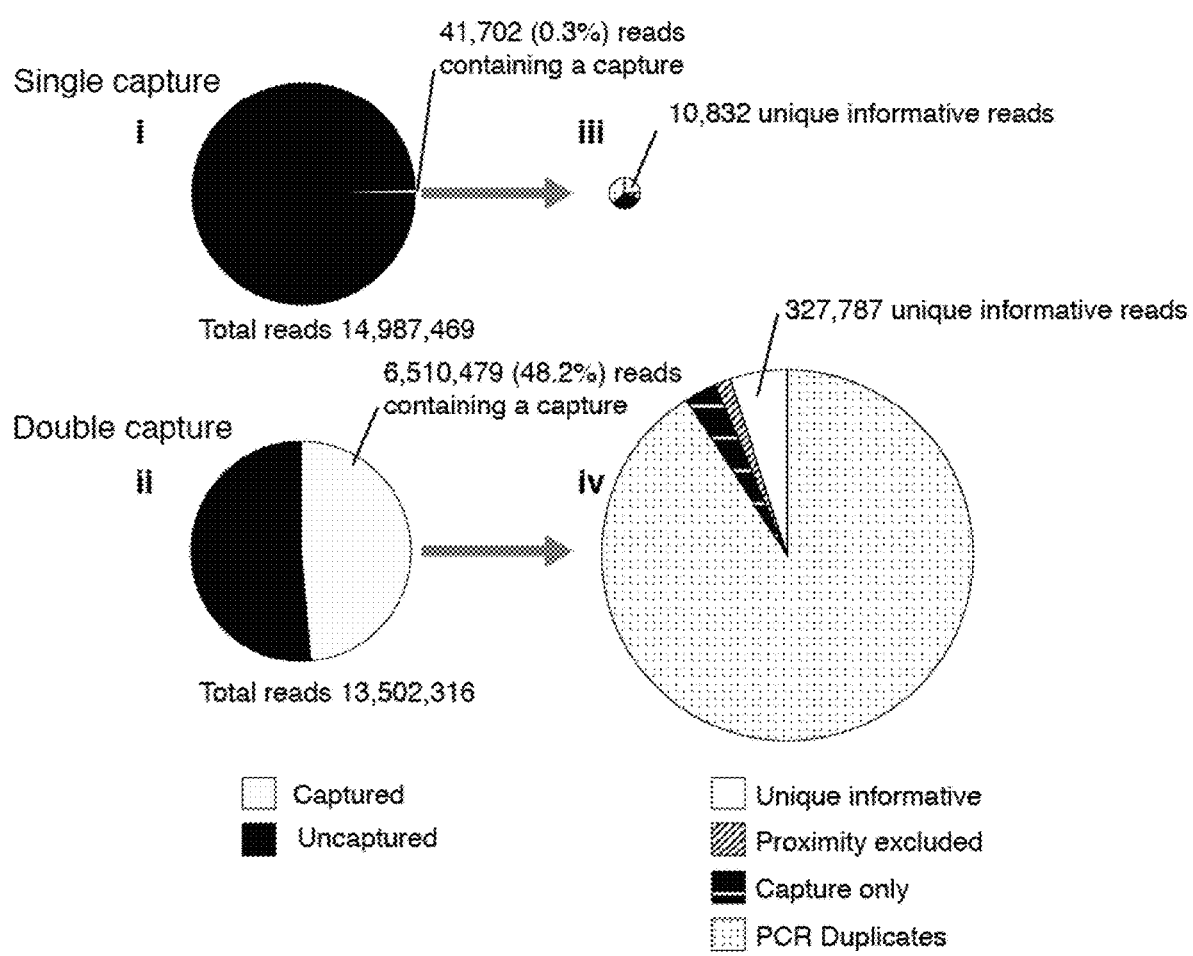
Figure 2:
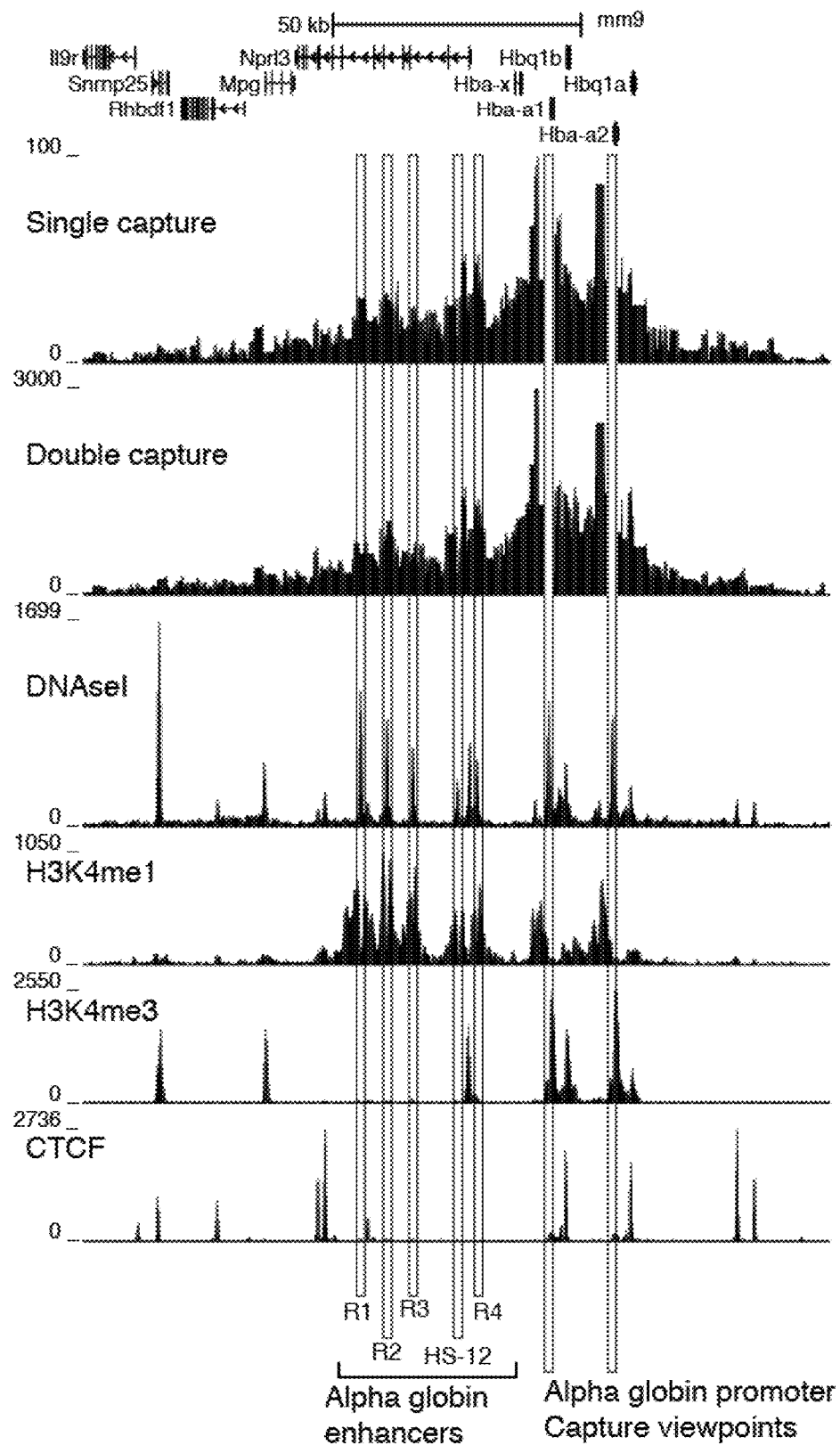

FIG. 2 illustrates a comparison of single and double oligonucleotide capture methods. 3C material generated from erythroid cells was captured using a single set of oligonucleotides designed to the alpha globin promoters. Since the two copies of the gene are virtually identical interaction profiles are generated from both genes simultaneously. After the first oligonucleotide capture step, some of the material was sequenced using the Illumina MiSeq. The remaining library was used as input for a second round of oligonucleotide capture and the resulting material was then sequenced.

a. Comparison of the enrichment (to scale) resulting from the single and double capture. (i) Single capture results in 5-20,000 fold enrichment but this only results in around 0.3% of the reads containing a sequence that maps to the captured fragment. (ii) Double capture increases the enrichment markedly, producing up to 3,000,000 fold enrichment. This dramatically increases the percentage of reads containing a restriction fragment that maps to the capture region from 0.3% to 48.6%. The number of unique interactions is increased around 30-fold following double capture (from 10,832 to 327,787) (iii & iv) because the library complexity now becomes the limiting factor.

b. Comparison of the raw informative interactions count per restriction enzyme fragment for single and double capture. The red vertical lines denote the location of captured viewpoints. The light blue lines highlight the five well described regulatory elements in the mouse (R1, R2, R3, R4 and HS-12). This shows that double capture does not significantly alter the local interaction profile but it has 30-fold increased sensitivity.

Figure 3:
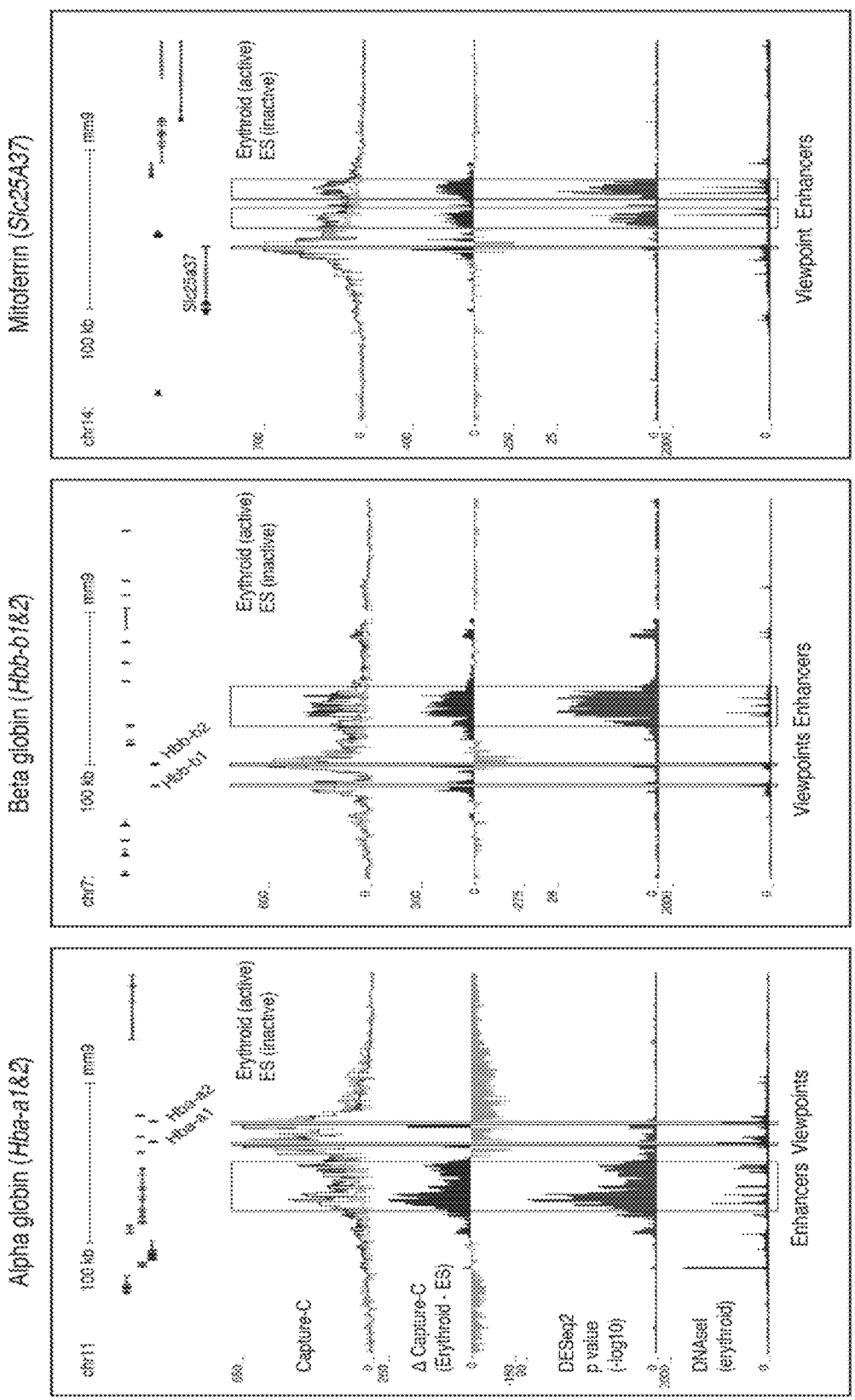

FIG. 3 illustrates high-resolution identification of regulatory element by comparative analysis between active and inactive states.

Top panel shows the overlaid normalized mean Capture-C profiles from erythroid (genes active in red) and ES cells (genes inactive blue) at three erythroid specific loci alpha globin, beta globin and Slc25A37 (Mitoferrin 1) in (erythroid n=4 and ES cells n=3). These data were generated along with the profiles for another 32 gene promoters simultaneously from seven samples in a single capture reaction (making a total of 245 interaction profiles from one oligonucleotide capture reaction). The Y-axis denotes the mean number of unique interactions per restriction fragment, scaled to a total of 100,000 interactions genome-wide.

The captured viewpoint fragments are highlighted in red and the interactions with the well-known enhancers as annotated by DNAseI hypersensitivity are highlighted as black hatched lines. The differential track (Δ Capture-C) shows that interactions with the local erythroid enhancers are clearly and specifically increased in erythroid cells when the genes are active. Below this DESeq2 analysis of the differential enrichment (minus $\log_{10}$ adjusted p values) mapped across the three loci shows the highly significant enrichment of the known regulatory interactions.

Figure 4:
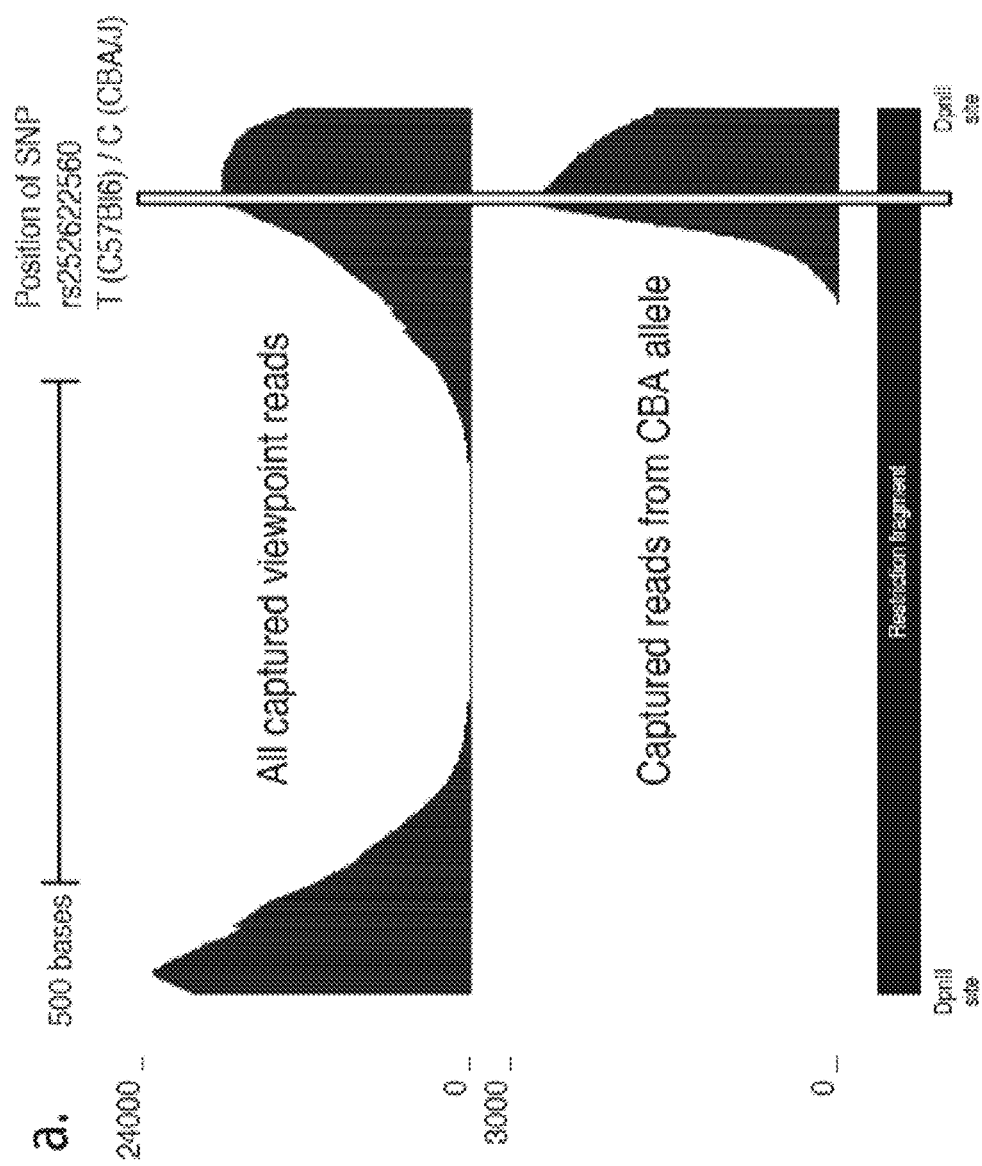
Figure 4:
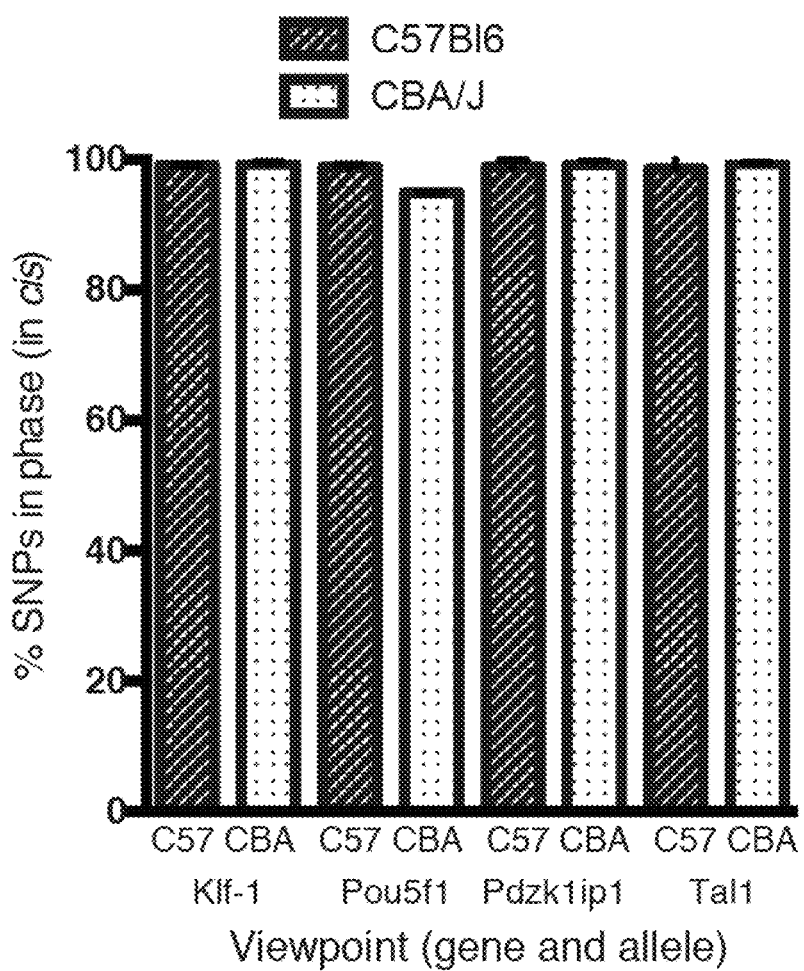
Figure 4:
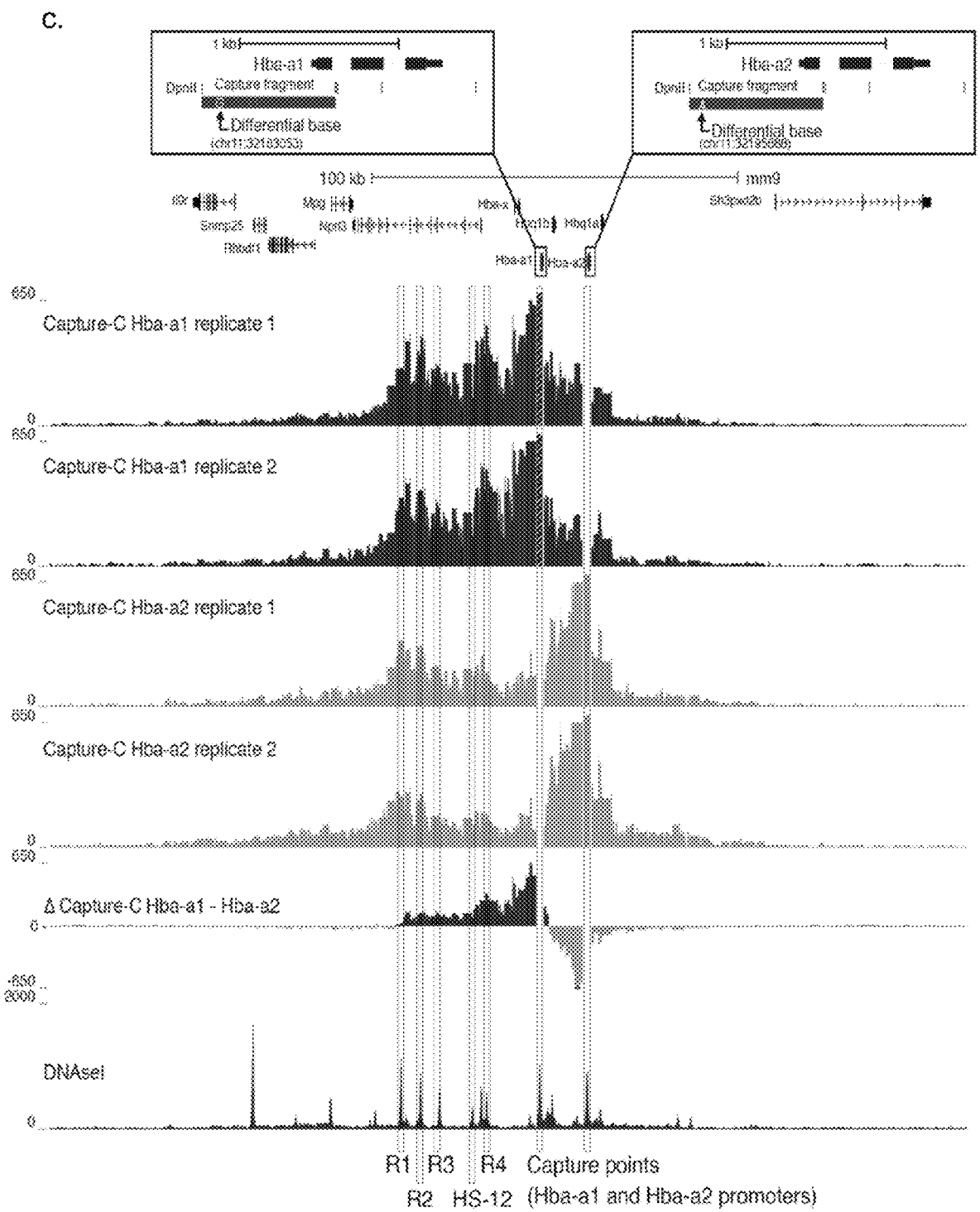

FIG. 4 illustrates SNP specific interaction profiles.

a. This shows a density plot of the reads mapping to the captured restriction fragment (the Tal-1 promoter fragment is shown). SNPs under the captured promoter allowed us to generate allele specific interaction profiles in F1 crosses between C57BL/6 and CBA/J mice. In the example locus, the SNP rs252622560 has been used to separate interactions from the two different alleles.

b. This shows a graphical representation of the % of SNPs in phase in the interacting reads compared with the strain of the captured allele in cis. This demonstrates that the chromosome predominately interacts with itself in cis rather than its sister chromatid.

c. SNP specific NG Capture-C has been used to generate specific interaction profiles for Hba-a1 and Hba-a2 parologous genes. A single nucleotide difference between the two genes allows generation of specific tracks (see inset). Hba-a1 is the more active of the two genes, producing around 70% of the total mRNA. Comparison of the two biological replicates shows that the SNP specific profiles are highly reproducible. The Δ Capture-C track shows the difference of the mean Hba-a1 and Hba-a2 profiles. This reveals that that the Hba-a1 gene preferentially interacts with the enhancers, particularly proximal HS-12 and R4 elements. The Hba-a2 gene interacts much more strongly with the chromatin between the two genes and interestingly it interacts with the most distal enhancer (R1) to a very similar degree to the Hba-a1 gene.

Figure 5:
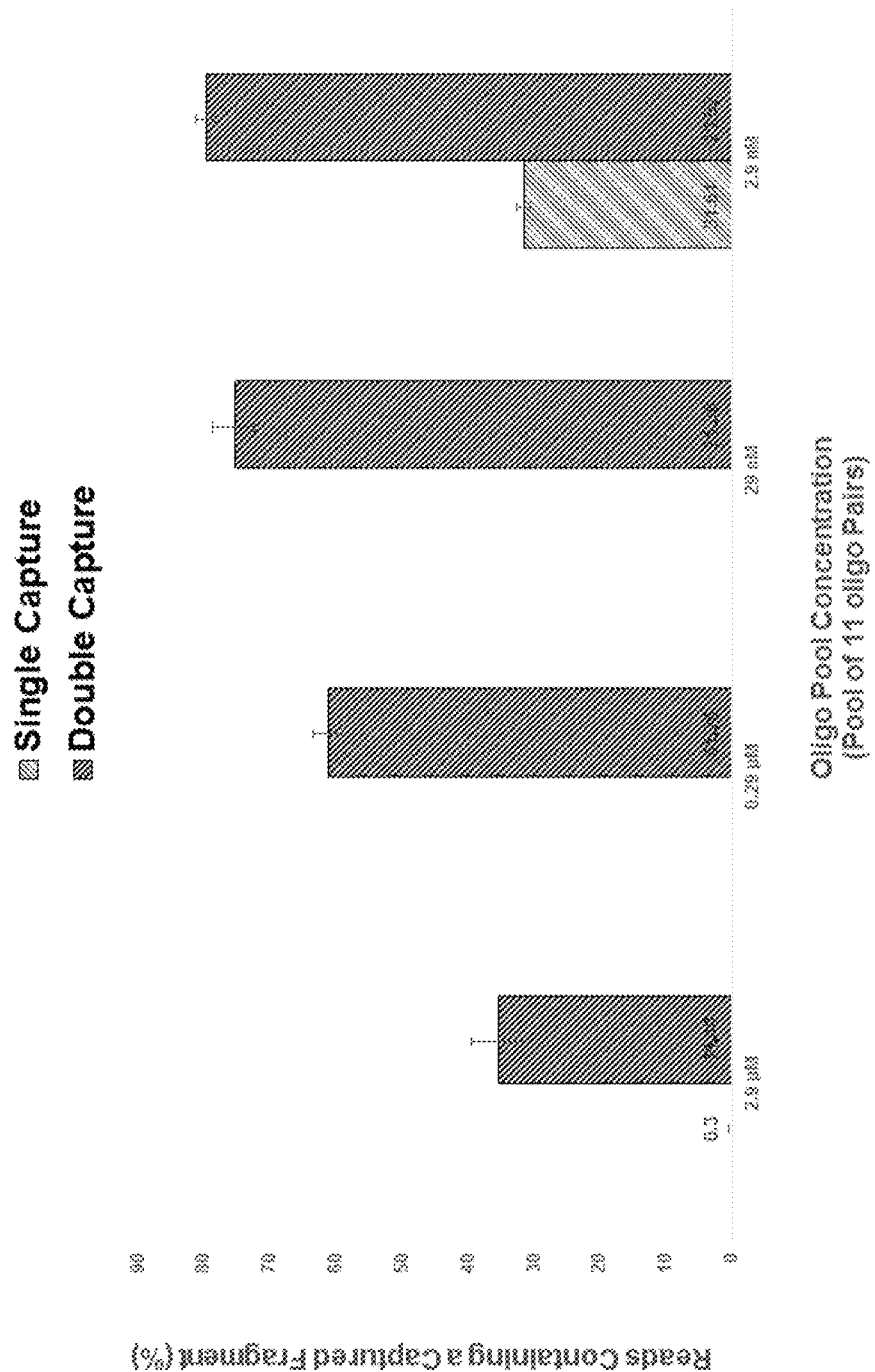

FIG. 5 illustrates decreasing the oligo pool concentration increases double-capture efficiency.

DETAILED DESCRIPTION OF THE INVENTION

One non-limiting example of an embodiment of the invention is illustrated in FIG. 1.

The invention relates to a method of identifying nucleic acid regions within a nucleic acid sample which interact with one another.

As used herein, the term "nucleic acid sample" encompasses chromatin, DNA and RNA. Preferably, the nucleic acid sample is DNA or chromatin, most preferably chromatin.

The nucleic acid sample may be obtained from any desired source.

For example, the nucleic acid sample may be obtained from prokaryotic or eukaryotic cells, or from viruses. Additionally, chromosomal DNA or plasmid DNA may be used.

The nucleic acid sample may be isolated or it may be in situ (e.g. within cells). Preferably, the nucleic acid sample is obtained from live cells.

In some preferred embodiments, the nucleic acid sample consists of 5-10,000 cells, preferably 100-10,000 or 1,000-10,000 cells. Preferably, the cells are eukaryotic cells, most preferably mammalian or human cells.

The nucleic acid regions which interact with one another are particularly DNA elements which affect or control the expression of an associated gene or other aspects of genome function or structure.

For example, the DNA elements may be promoters, enhancers, insulators and/or silencers.

As used herein, the term "3C library" refers to a library of DNA fragments, wherein the DNA fragments comprise contiguously-joined DNA elements wherein the DNA elements are ones which are capable of interacting with one another (for example within a cell).

In some embodiments of the invention, the method relates to a 3C library which has been produced by the following steps. In other embodiments of the invention, the method includes the following steps of producing the 3C library.

Preferably, the 3C library is or has been produced by the steps of:
(i) cross-linking a nucleic acid sample;
(ii) fragmenting the cross-linked nucleic acid sample to produce nucleic acid fragments;
(iii) ligating the nucleic acid fragments to produce ligated nucleic acid fragments; and
(iv) de-crosslinking the ligated nucleic acid fragments.

In some preferred embodiments of the invention where the nucleic acid sample is chromatin, the 3C library is or has been produced by the steps of:
(i) cross-linking a chromatin sample;
(ii) fragmenting the cross-linked chromatin sample to produce chromatin fragments;
(iii) ligating the chromatin fragments to produce ligated chromatin fragments; and
(iv) de-crosslinking the ligated chromatin fragments.

Step (i) comprises cross-linking the nucleic acid sample.

In this step, the sample of nucleic acids (e.g. chromatin) is cross-linked such that regions of nucleic acids within the nucleic acid sample (e.g. chromatin) which were interacting with one another are held or fixed in close proximity.

The regions of nucleic acids within the nucleic acid sample (e.g. chromatin) which were interacting with one another may be cross-linked directly (i.e. nucleic acid to nucleic acid) or indirectly (e.g. by cross-linking of the nucleic acids to moieties (e.g. proteins) which are bound to the nucleic acids).

Preferably, the nucleic acid sample is cross-linked using a cross-linking reagent. Preferably, the cross-linking agent is formaldehyde.

Step (ii) comprises fragmenting the cross-linked nucleic acid sample (e.g. chromatin) from Step (i) to produce nucleic acid fragments. The nucleic acid fragments are preferably chromatin or DNA fragments.

In this step, the cross-linked nucleic acid sample (e.g. chromatin) is fragmented in order to remove stretches of nucleic acids which are situated a large distance away (e.g. more than 1 kb) from the position of crosslinking. (The subsequent ligation rearranges the order of the nucleic acid fragments so they then reflect their proximity in 3 dimensional space rather than their original proximity in the linear nucleic acid molecule.) The fragmenting step introduces free ends in the nucleic acid fragments at positions which are near to the positions of cross-linking.

For example, the fragmenting step may result in nucleic acid fragments wherein at least 50% of the fragments are less than 1000 base pairs in length, preferably less than 800, 600 or 400 base pairs in length (when measured from a free end to a point of cross-linking with another nucleic acid).

The fragmenting step should preferably not affect the integrity of the cross-linking or not substantially affect the integrity of the cross-linking.

The fragmenting may be carried out by any suitable manner. Examples of fragmenting processes include using sonication and using endonucleases.

Preferably, the fragmenting is carried out using restriction endonucleases, most preferably using restriction endonucleases which recognise 4 base pairs (e.g. Dpn II or Nla III).

In some embodiments of the invention, the fragmentation step does not comprise the step of labelling the free ends of the nucleic acid fragments with the first half of a binding pair. In particular, in some embodiments of the invention, the fragmentation step does not comprise the step of labelling the free ends of the nucleic acid fragments with biotin.

Step (iii) comprises ligating the nucleic fragments obtained from Step (ii) to produce ligated nucleic acid fragments. The ligated nucleic acid fragments are preferably ligated chromatin fragments or ligated DNA fragments.

In this step, the free ends of the nucleic acid fragments which were produced in Step (ii) are ligated together in order to produce ligated nucleic acid fragments.

Ligation will occur in a random manner between the free ends of the nucleic acid fragments. However, ligation will occur most preferably between adjacent free nucleic acid ends which are held in close proximity to one another by the cross-linking process of Step (i). In this way, regions of nucleic acid within the nucleic acid sample which previously interacted with one another will now preferably become chemically joined (ligated) to one another.

The length of the ligated nucleic acid fragments may be controlled by varying the ligation conditions (e.g. duration of ligation).

Preferably, the ligated nucleic acid fragments are more than 20 kb in length or 1-20 kb or 5-15 kb in length, and most preferably about 20 kb in length.

Ligation may be carried out using any suitable ligating agent, e.g. a ligase. Preferably, the ligase is a DNA ligase. Examples of suitable DNA ligases include T4 DNA ligase.

In Step (iv), the ligated nucleic acid fragments are de-crosslinked. In this step, the ligated nucleic acid fragments (e.g. ligated chromatin fragments) are uncrosslinked in order to produce linear nucleic acid fragments (e.g. linear chromatin fragments). For example, the crosslinking moieties are cleaved or removed.

In some embodiments, the crosslinks are removed by heating the ligated nucleic acid fragments to a high heat, such as to 50° C., 60° C., 70° C., 80° C. or greater. The decrosslinking may also be carried out using Proteinase K.

Optionally, non-nucleic acid material (e.g. proteins, cross-linking agents, etc.) is also removed at this time.

For example, the ligated nucleic acid fragments may be extracted with phenol/chloroform.

In Step A, the nucleic acid fragments in a 3C library are fragmented. The nucleic acid fragments are preferably DNA fragments. In this step, the lengths of the nucleic acid fragments in the 3C library are reduced to a size which is suitable for capture and amplification. Preferably, the lengths of the nucleic acid fragments are reduced to 100-500 base pairs, more preferably 100-300 or 150-250 base pairs, and most preferably to about 250 base pairs.

Fragmentation may be performed by any suitable process. Examples of suitable fragmentation processes include using nucleases (e.g. restriction endonucleases) and sonication. Preferably, the fragmentation is by sonication.

In Step B, sequencing adaptors are optionally added to the ends of the nucleic acid fragments. Furthermore, the nucleic acid fragments may be amplified at this time. In this optional step, sequencing adaptors and/or amplification primers (e.g. short double-stranded nucleic acids) are added to both ends of the nucleic acid fragments in order to facilitate the amplification and later sequencing of the nucleic acid fragments.

Each sequencing adaptor may comprise a unique indexing barcode, i.e. a short nucleic acid motif which acts as a unique identifier for that nucleic acid fragment. Preferably, the sequencing adaptors are Next Generation sequencing adaptors. In some embodiments, the sequencing adaptors comprise P5 or P7 sequences.

The sequencing adaptors may be added to the nucleic acid fragments by ligation-mediated PCR.

In some embodiments, the sequencing adaptors are added using "tagmentation" (transposome mediated fragmentation) using a transposase, e.g. the mutated hyperactive transposase Tn5. The TN5 transposase is one of the first transposases discovered and is very well studied. Its highly efficient "cut and paste" action on DNA has been selectively modified to produce an enzyme with minimal sequence specificity that has been is now used as a molecular tool to fragment DNA while efficiently adding DNA sequences and in particular for creating next generation sequencing libraries for genome sequencing, referred to as "tagmentation". Subsequently, it has also been exploited to efficiently probe features of the genome such chromatin accessibility in low cell numbers [37].

The sensitivity of the assay is dependent on the efficiency with which the ligation events in the 3C library can be sampled. Importantly, the number of cells that are required to generate an interpretable signal is dependent on the sensitivity of the assay. One of the most inefficient steps in all NGS (Next Generation Sequencing) protocols is the addition of the sequencing adapter because an appropriate adapter has to be added to both ends of the fragmented DNA sequence; any fragment which fails to have both adapters ligated is lost to the assay.

When cell numbers are very limited, such as in human primary tissues, it is important to make sure that as many fragments as possible are included in the assay to sample the small number of cells at the highest possible depth per cell. Unlike other 3C methods, Capture-C and its derivative such as Capture Hi-C use fragmented DNA. This allows for the use of a very efficient method of adapter addition, namely "tagmentation".

Tagmentation not only fragments the DNA, it also adds DNA adapters at the same time; hence a fully fragmented sample should all have adapters. Although typically only 50% will have the adapters in the correct combination (A+B, or B+A rather than A+A or B+B) it is still much more efficient than ligation-based methods. A unique feature of Capture can be used to make this even more efficient. As the fragmentation of the 3C library produces unique ends, PCR duplicates are easily identified. Therefore a single adapter sequence can be used in the tagmentation reaction which will amplify all fragments and can be amplified such that all fragments are duplicated many times. At this point, the A+B sequences required for sequencing can be added by PCR using primers that can prime off the common primer at the ends of the fragments. This will still only be 50% efficient (A+B, or B+A rather than A+A or B+B). However, as the fragments are now duplicated, multiple versions will always be available for sequencing.

The nucleic acid fragments may also be amplified (e.g. by PCR) at this time. For example, 1-20 rounds of PCR may be performed, preferably 3-10 rounds and most preferably about 6 rounds of PCR.

The indexed samples may optionally now be pooled for multiplex sequence analysis.

In Step C, the nucleic acid fragments are contacted with a targeting nucleic acid which binds to a subgroup of the nucleic acid fragments, wherein the targeting nucleic acid is labelled with the first half of a binding pair. In this step, the desired nucleic acid fragments (e.g. DNA fragments) are prepared for isolation from the background of contaminating nucleic acid fragments.

A targeting nucleic acid is used which has a nucleotide sequence which is complementary or substantially complementary to that of a desired region of the nucleic acids within the nucleic acid sample. The targeting nucleic acid will therefore hybridise, under appropriate conditions, to the desired region of the nucleic acid within the nucleic acid sample.

For example, the desired region of the nucleic acid may be that of a promoter from a particular gene (wherein it is desired to determine which DNA regions interact with that promoter) or it may be that of an enhancer element (wherein it is desired to determine which genes are enhanced by that element).

The targeting nucleic acid may be single- or double-stranded, preferably single-stranded. The targeting nucleic acid may be DNA or RNA, preferably DNA (e.g. a DNA oligonucleotide).

When a restriction endonuclease is used in the production of the 3C library, the targeting nucleic acid preferably contains the ends of the restriction fragment containing the desired region and includes the restriction endonuclease site. In this way, the targeting nucleic acid binds to informative ligation junctions.

Preferably, the concentration of the targeting nucleic acid (e.g. a DNA oligonucleotide) is 5 µM to 1 pM. More preferably, the concentration of the targeting nucleic acid (e.g. a DNA oligonucleotide) is 2.9 µM to 29 pM. Even more preferably, the concentration of the targeting nucleic acid (e.g. a DNA oligonucleotide) is 1 µM to 30 pM, or 300 nM to 30 pM. Even more preferably, the concentration of the targeting nucleic acid (e.g. a DNA oligonucleotide) is 30 nM to 0.3 nM. Most preferably, the concentration of the targeting nucleic acid (e.g. a DNA oligonucleotide) is about 2.9 nM.

Examples of binding pairs include biotin with streptavidin. Preferably, the first half of the binding pair is biotin.

In Step D, the second half of the binding pair is used to isolate the subgroup of nucleic acid fragments which have been bound by the targeting nucleic acid. In this step, the second half of the binding pair is allowed to bind to the first half of the binding pair. In order to aid isolation of the targeted nucleic acid fragments, the second half of the binding pair may be bound to a physical support, for example a column or a bead (e.g. a magnetic bead).

For example, the first half of the binding pair may be biotin and the second half of the binding pair may be a streptavidin-coated bead. The targeted nucleic acid fragments may then be isolated from the background by virtue of the fact that they will be bound to the column or magnetic beads, wherein the background nucleic acids may then be removed.

In some embodiments of the invention, the method is not carried out on a microarray.

In Step E, the isolated subgroup of nucleic acid fragments are amplified. In this step, the isolated nucleic acid fragments (e.g. DNA fragments) are amplified in order to enrich the desired nucleic acid fragments.

Preferably, the amplification is by PCR. Preferably, the amplification comprises 10-40 cycles of PCR amplification, more preferably 14-18 cycles.

In the embodiments of the invention wherein the sequencing adaptors comprise P5 or P7 sequences, PCR primers which bind to the latter sequences may be used.

Steps A-E of the method of the invention may result in an enrichment of approximately 5-20,000 fold over the corresponding method without Steps C, D and E.

In Step F, Steps C, D and E are repeated (in this order). This results in an enrichment of the desired nucleic acid fragments of approx. 3,000,000 fold over the corresponding method without Steps C, D, E and F.

Steps C, D and E may be repeated (in this order) one or more times, e.g. 1, 2, 3, 4 or 5 times, preferably 1 or 2 times.

Optionally, the method additionally comprises Step G, i.e. sequencing the amplified subgroup of nucleic acid fragments. The skilled person will be well aware of numerous DNA sequencing methods which may be used. Preferably, the sequencing is performed using Illumina Miseq (150 pb, pair end) or Hiseq (100 bp, pair end).

Steps A-G are carried out in the order specified.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. The disclosure of each reference set forth herein is incorporated herein by reference in its entirety.

Example 1: Preparation of 3C Libraries

Single cell preparations of erythroid cells were made by gently dissociating cells from the spleen of a mouse treated with phenylhydrazine (40 mg/g body weight×3 doses 12 h apart; sacrificed on day 5). Phenylhydrazine causes haemolytic anemia and marked erythroid expansion in the spleen so that 80% or more of cells are erythroid cells (as defined by CD71+ ter119+). The cells were passed through a 40 µm cell strainer to remove clumps. For ter119 selection, cells were stained with ter119-phycoerythrin (PE) and purified using anti-PE MACS beads (Miltenyi Biotec) prior to fixation with formaldehyde. Mouse E14 ES cells were trypsinised and washed once prior to fixation.

Each aliquot of $10^7$ cells was resuspended in 10 ml of RPMI with 10% FCS in a 15-ml conical centrifuge tube. 549 µl 37% (vol/vol) formaldehyde was added to each aliquot to make an overall concentration of 2% (vol/vol). A 10 minute incubation was performed at room temperature on a roller mixer. The crosslinking reaction was then quenched with 1.5 ml cold 1M glycine and the sample was centrifuged immediately for 5 min at 220 g in a precooled centrifuge at 4° C. The supernatant was discarded and the pellet was gently resuspended in 10 ml cold Phosphate Buffered Saline (PBS). The cells were centrifuged again (5 min 220 g 4° C.) and the supernatant discarded. The pellet was resuspended in 5 ml cold lysis buffer and incubated on ice for 20 min. The nuclei were centrifuged (5 min, 500 g, 4° C.) and the supernatant carefully removed. Multiple aliquots can be snap frozen using liquid $N_2$ or dry ice and ethanol and stored for several months at −80° C. Cells were resuspended in 1 ml water (MilliQ or Sigma) and Dounce homogenised (45 strokes; 5 ml Dounce homogeniser) on ice. The sample was pelleted (5 min, 22,000 g, 4° C.) and resuspended to a total of 650 µl water (Milli-Q or Sigma). Three reactions were set up for each sample in 1.5 ml Eppendorf Safe-Lock microcentrifuge tubes. Each digestion reaction was made up of 200 µl cell suspension; 80 µl of ×10 restriction enzyme buffer; 10 µl SDS 20% (vol/vol) and water to make a final volume of 800 µl after the later addition of 66 µl Triton X-100 and restriction enzyme. A control reaction to check for nonspecific digestion (final volume 200 µl) was also set up in a 1.5 ml Eppendorf tube. This included 50 µl cell suspension; 40 µl×10 restriction enzyme buffer; 2.5 µl SDS 20% (vol/vol) and 111 µl water, making a total of 200 µl after the addition of Triton X-100. All reactions were placed on a thermomixer (Eppendorf) for 1 h at 37° C. shaking at 1400 r.p.m. 66 µl Triton X-100 was added to each of the digestion reactions and 16 µl to the control reaction followed by an incubation of 1 h on the thermomixer (37° C. 1400 rpm). Three aliquots of 500 U restriction enzyme were added to each digestion reaction several hours apart. The samples were incubated on the thermomixer (37° C., 1400 rpm) for 16-24 h after the initial dose of restriction enzyme.

100 µl was removed from each digestion reaction and pooled to make a control to assess digestion. The DNA was extracted from the two controls using a standard phenol/chloroform extraction (including proteinase K and RNAse steps).

The restriction enzyme in the digestion reactions was heat inactivated by incubating at 65° C. for 20 mins. The samples were then cooled on ice and 500 µl water (Sigma); 133 µl×10 ligation buffer and 8 µl high concentration T4 DNA ligase (Thermoscientific, 30 U/µl) was added to each digestion reaction. The samples were then agitated at 1400 r.p.m. overnight using the thermomixer at 16° C.

To decrosslink the ligated material, 5 µl Proteinase K (Thermoscientific >600 U/ml) was added to each reaction and incubated at 65° C. overnight. The three reactions were pooled in a 15 ml conical centrifuge tube; 30 µl RNAse (Roche) was added prior to an incubation at 37° C. for 30 min. DNA was purified from the reaction using a phenol chloroform extraction ((4 ml) of phenol/chloroform/isoamyl alcohol (25:24:1)/4 ml chloroform). The DNA was precipitated in a large volume to improve removal of DTT.

The 4 ml sample was placed in a 50 ml tube with 7 ml water (Milli-Q); 1.5 ml 2M sodium acetate and 35 ml 100% ethanol. The samples were frozen (−80° C. for at least 2 h) and centrifuged at 20,000 g for 30 min at 4° C. The pellet was then washed with 10 ml 70% ethanol dry and dried room temperature prior to being reconstituted in PCR grade water. This '3C library' can be stored at −20° C. for several months.

3C Library Controls

To determine the efficiency of digestion and ligation and check for non-specific digestion 10 µl of each control and 5 µl of the 3C library was run on a 1% (wt/vol) agarose gel. The digestion efficiency was also checked using qPCR with primers designed across one of the restriction enzyme digestion sites at the alpha globin promoter (DpnII digestion control) and another primer set that lies close to the other end of the same restriction fragment (Hba-a1&2 control primer). Digestion efficiencies were always in excess of 70% for libraries used for analysis. The concentration of DNA in the 3C library was determined using Qubit (BR).

Real Time Primers for Assessing Digestion

```
DpnII digestion control forward primer
                                     (SEQ ID NO: 1)
GTGTCACCAAAACCAGCTCA.

DpnII digestion control reverse primer
                                     (SEQ ID NO: 2)
CCTGGAATCCTTTGGCTCAAG.

DpnII digestion control Taqman probe
                                     (SEQ ID NO: 3)
GGGCAGCTAAGATGCAAGTC.

Hba-a1 & 2 control forward primer
                                     (SEQ ID NO: 4)
TGGAGGGCATATAAGTGCTACTTG.

Hba-a1 & 2 control reverse primer
                                     (SEQ ID NO: 5)
TGCTTTTGTCTTCCCCAGAGA.

Hba-a1 & 2 control Taqman probe
                                     (SEQ ID NO: 6)
TGCAGGTCCAAGACACTTCTGATTCTGACA.
```

Example 2: Addition of Sequencing Adaptors

5 µg of 3C library was sonicated to 200 bp using a Covaris S220 Focussed ultrasonicator (6 cycles of 60 s: duty cycle 10%; intensity 5; cycles per burst 200). The degree of sonication was confirmed using an Agilent Bioanalyser or Tapestation (DNA 1000). Illumina Truseq indexed sequencing adapters were added using NEBnext reagents (E6000/E6040/E7335/E7500). This involved end repair, addition of overhanging A bases, ligation of adapters and PCR to add the indices. The DNA was cleaned up between reactions using Ampure XP beads at a 1:1.8 ratio for all clean up steps to minimize the selection of larger fragments and losses of material were minimised. 6-8 cycles of PCR were used when addition the Truseq indices using the Agilent Herculase II PCR kit. Generally 1.5-2 µg of adapter ligated material was generated, however, to maximize library complexity the library preparation was usually done in duplicate (to use 10 µg of input material) and the samples were pooled. The libraries were analysed using an Agilent Bioanalyser or Tapestation (DNA 1000) both pre- and post the PCR and addition of sequencing adaptors as this allowed the DNA losses (and library complexity) to be assessed prior to amplification.

Biotinylated DNA oligonucleotides (IDT ultramers or Sigma long synthesis) were reconstituted to a concentration of 2.9 µM. This allowed different oligonucleotides to be mixed in equimolar quantities so that 4.5 µl of the resulting library would always contain a total of 13 pmol of oligonucleotide pool. These oligonucleotides are vastly in excess in the hybridization reaction so that contamination with very small quantities can results in significant capture, which can lead to spurious results. We recommend that oligonucleotides for different experiments are ordered from the manufacturer and handled separately as contamination can occur during the manufacturing process.

Example 3: Oligonucleotide Capture 1.5-2 µg of adapter ligated material was placed in a 1.5 ml microcentrifuge tube with 5 µg COT DNA from the appropriate species; 1000 pM Nimblegen HE Universal blocking oligo and 1000 pM Nimblegen HE Index specific blocking oligo (corresponding to the Illumina TS index used). The sample was then dried using a vacuum centrifuge (50-60° C.) until no liquid remained. The residue was dissolved in 7.5 µl Nimblegen Hybridization Buffer and 3 µl Nimblegen Hybridization Component A followed by denaturation at 95° C. for 10 minutes. Concurrently 4.5 µl of the biotinylated capture oligonucleotide library (total 13 pM) was heated to in a 0.2 ml PCR tube to 47° C. in a PCR block. After 10 minutes the 3C library and blocking oligonucleotides were added to the preheated biotinylated oligonucleotides at 47° C. The hybridization reaction was incubated in a PCR machine at 47° C. for 64-72 h (with a heated lid at 57° C.).

The Nimblegen SeqCap EZ Wash Buffers (I, II, III, Stringent and Bead Wash Buffers) were prepared and where necessary preheated to 47° C. using the thermomixer. 100 µl M270 streptavidin beads were aliquoted into a 1.5 ml microcentrifuge tube and allowed to warm to room temperature for 30 min. Two washes with 200 µl Bead Wash Buffer were performed, using a DynaMag device to capture the beads and allow the supernatants to be discarded. After the final wash the hybridization reaction was added directly to the beads and mixed thoroughly by pipetting up and down and vortexing. The samples were put into the thermomixer at 47° C. and mix at 500 rpm for 45 minutes. After 45 minutes, 100 µl of Wash Buffer I, heated to 47° C., was added and the samples were mixed by vortexing for 10 seconds. The tube was placed in a DynaMag device and the liquid discarded once it became clear. 200 µl Stringent Wash Buffer, heated to 47° C., was added and mixed before incubating at 47° C. for 5 minutes. The tube was then put into a DynaMag device and the liquid was discarded once it became clear. This step was repeated twice so that two washes were performed with Stringent Wash Buffer. 200 µl of Wash Buffer I was added to the sample at room temperature and it was mixed by vortexing for 2 mins. The tube was then returned to the DynaMag device and the liquid discarded once it had become clear. 200 µl of Wash Buffer II was added and mixed by vortexing for 1 minute. Then the tube was returned to the DynaMag device and the liquid discarded. The beads were then resuspended in 200 µl of Wash Buffer III and the sample was mixed by vortexing for 30 seconds. The tube was replaced in the DynaMag device and the liquid discarded once it became clear. The beads were resuspended in 40 µl of PCR grade water (the beads can be stored at −15 to −25° C. at this point). The captured material was PCR amplified directly from the beads using either the SeqCap EZ Post-Capture LM PCR Master Mix and Post LM-PCR oligos (×18 cycles) or the newer Kappa master mix supplied in the SeqCap EZ accessory kit v2 (×14 cycles). An Ampure-XP bead clean up was then performed and the captured material removed from the beads using 30 µl PCR grade water (Sigma). The captured material was assessed using the Agilent Bioanalyser or Tapestation.

This material was then used as input for the second round of oligonucleotide capture. The hybridization reaction was set up as for the first capture although less input material was used. 75% of the material up to a total of 2 µg was used for the second hybridisation reaction since it is likely that thousands of copies of each captured ligation junction are present in the library by this point. For the second round of capture the material was only hybridized for 24 h rather than 64-72 h. The bead washes and PCR amplification of the material were identical to the first capture.

Following the second capture the mass of captured material was assessed using the Agilent Bioanalyser or Tapestation and Qubit. A 4 nM solution (the concentration required for loading the Illumina MiSeq) was made using the size of the fragments assessed by the Bioanalyser or Tapestation and the concentration measured by the Qubit. Oligonucleotide capture enrichment can be determined by real time PCR, using the Hba-a1&2 control primers above and a standard curve of genomic DNA to compare to the concentration of the input material determined by Qubit.

Example 4: Multiplexed Library Capture

Multiple samples can be captured simultaneously by labelling them with different index adaptors and mixing prior to the oligonucleotide hybridization. In order to maintain library complexity, for the first capture, 1-2 µg from each sample was pooled in an exact 1:1 stoichiometry. It is important to do this precisely as the percentage of reads obtained from each sample will be directly related to the amount of DNA mixed. 5 µg COT DNA and 1000 pmol of universal TS HE blocking oligonucleotides were added for each sample and 1000 pmol of the index specific blocking oligonucleotide was added for each sample. The mixture can then either be split into multiple identical hybridization reactions each of the same volume of a single sample or one large hybridization reaction can be made. The hybridisation, streptavidin bead capture and wash protocols were followed as outlined above, except that the volumes were adjusted appropriately when larger volume captures were undertaken. The PCR reactions were performed using the same volumes as for a single capture (multiple reactions were performed in parallel). For the second capture, the material was pooled from all of the PCRs and a single second capture was performed on this material. It is possible to use a single volume capture at this point because the library should contain thousands of copies of each captured read and so it is unlikely significant complexity will be lost during the second capture.

Example 5: Sequencing

A 4 nM solution of the libraries was made using the fragment size from the bioanalyser or tapestation and the overall concentration measured by the Qbit. The concentration can also be confirmed using real time PCR (SYBR green) with the P5 and P7 sequences on the adaptors. The majority of material was sequenced using the Illumina Miseq (300 bp V2 chemistry), which produced 10-20 million 150 bp paired end reads depending on the cluster density. One larger experiment was sequenced on the Illumina HiSeq producing 100 bp paired end sequences.

Example 6: Adaptations for Reduced Cell Numbers

The 3C library preparation was performed as above with the following adaptations: a) the volume of the digestion reaction was reduced to 200 µl for 3 million cells or less and 50 µl for 500,000 cells or less. When less than 1 million cells were used to save material the two control samples were omitted and digestion efficiency was assessed on the ligation reaction using real time PCR. The CT value for the ligation reaction is nearly identical to the digestion control because the probability of the fragment ligating back to its original position appears negligible compared to the proportion of undigested material. The entire library preparation was performed in a single 1.5 ml Eppendorf tube to minimize losses. The phenol-chloroform extraction was performed as above except that the DNA precipitation was performed in a smaller volume (×3 volume 100% ethanol; $\frac{1}{10}^{th}$ volume NaOAC 2M; 1 µl glycogen (Invitrogen) as carrier). All of the material was sonicated to 200 bp and sequencing adaptors were added using the NEBnext Ultra DNA library prep reagents (E7370). Additional PCR cycles were used to compensate for the smaller quantities of DNA (10 cycles for 500,000 cells/12 cycles for 100,000 cells). Following this the material underwent a double oligonucleotide capture as outlined above.

Example 7: Data Analysis

Initially the adaptor sequences are removed from the reads in the raw FASTQ files using Trim_galore (a wrapper tool around Cutadapt and FastQC; Babraham Institute http://www.bioinformatics.babraham.ac.uk/projects/trim_ga-lore/). This is particularly necessary when using 150 bp paired end sequencing because some of the reads are shorter than 150 bp and the sequence will extend into the adaptor. The paired end reads were then reconstructed into single reads, where possible using FLASH with interleaved output settings[34]. These two steps can be omitted when shorter reads are used that do not have an area of central overlap and instead a file of these reads is generated with the paired end reads interleaved in strict order (read 1 FASTQ followed by read 2). An in silico restriction enzyme digestion of the reads was then performed using the script (DpnII2E.pl https://github.com/telenius/captureC/releases) with the name of the read being used to keep a record of each sub-fragment. The resulting FASTQ file of sub-fragments was then aligned using bowtie1 (using P1, M2, best and strata settings). Fragments that result from non-specific ligation and do not contain the restriction cut sequence will not be mapped to the genome by bowtie 1 and are therefore discarded. It is important that the reads are in strict order for the subsequent analysis, which can be achieved either by sorting based on the name or using one processor for the alignment.

The resulting sam file is then analysed with the main script CCanalyser2.pl (https://github.com/telenius/captureC/releases). This classifies the sub-fragments as either being: a) "capture" if they are contained within the capture fragment; b) "proximity exclusion" if they are inside the defined proximity exclusion coordinates (usually 1 kb on either side of the capture fragment) or c) "reporter" if they are outside of all of the capture and proximity exclusion regions in the entire experiment. PCR duplicates were excluded by removing reads that had the same start and end coordinates of each sub-fragment. For long-range cis and trans analysis the start and stop coordinates of the interacting read itself also had to be unique. This more stringent filter was used to remove PCR duplicates because occasionally sequencing errors in the captured restriction fragment allowed PCR duplicates to appear unique. Unique interactions were only reported when the read was unique and there were one or more "reporter" and a single "capture" subfragment defined from a single read.

CCanalyser2.pl can map the reads either to the whole restriction enzyme fragment or, to give the maximum resolution possible, they can be mapped to the half fragment based on the midpoint of the read and restriction fragment.

CCanalyser2.pl is also capable of creating SNP specific tracks, in which a specific base has to be present at a specific position in the capture fragment for the data to be included.

The data are then filtered to remove regions with problematic mappability due to copy number differences and mismapped reads from the proximity exclusion region. The latter was achieved by mapping the sequence of the proximity exclusion zone back to the genome using BLAT. Restriction fragments outside of 2 Mb from the viewpoint (this was chosen so that gene duplications, such as Hba-a1&2 were not excluded) were excluded if the proximity exclusion zone mismapped to them. The read count per fragment was normalized to the total number of reads in the track to give the number interactions per 100,000 interactions in the whole track using R. These data were subsequently converted to a format suitable for viewing in the UCSC genome browser (http://genome.ucsc.edu/)[35, 36].

Statistical analysis was performed using DESeq2[24]. Unnormalised raw counts per restriction fragment were used for this analysis and restriction fragments with no reads mapping to them were excluded from the analysis.

Example 8: Decreasing the Oligo Pool Concentration Increases Double-Capture Efficiency The effectiveness of capture from targeted regions (expressed as percentage of sequence reads from targeted region within the sequenced pool) was tested across 11 regions. FIG. 5 shows the average performance of the 11 test regions across 4 effective probe concentrations on the X axis and the capture efficiency after single- and double-capture at each concentration (left and right hand columns, respectively, for each concentration). It can be see that an oligo concentration of 2.9 nM increases specificity up to 85-95% after double-capture.

The previous detailed description is of a number of embodiments for implementing the invention; this is not intended to be limiting in scope. Once of skill in this art will immediately envisage the methods and variations used to implement this invention in other areas than those described in detail.

REFERENCES

1. Wang, Z., Gerstein, M. & Snyder, M. RNA-Seq: a revolutionary tool for transcriptomics. Nat Rev Genet 10, 57-63 (2009).
2. Mikkelsen, T. S. et al. Genome-wide maps of chromatin state in pluripotent and lineage-committed cells. Nature 448, 553-60 (2007).
3. Robertson, G. et al. Genome-wide profiles of STAT1 DNA association using chromatin immunoprecipitation and massively parallel sequencing. Nat Methods 4, 651-7 (2007).
4. Hesselberth, J. R. et al. Global mapping of protein-DNA interactions in vivo by digital genomic footprinting. Nat Methods 6, 283-9 (2009).
5. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nat Methods 10, 1213-8 (2013).
6. Dekker, J., Rippe, K., Dekker, M. & Kleckner, N. Capturing chromosome conformation. Science 295, 1306-11 (2002).
7. Tolhuis, B., Palstra, R. J., Splinter, E., Grosveld, F. & de Laat, W. Looping and interaction between hypersensitive sites in the active beta-globin locus. Mol Cell 10, 1453-65 (2002).
8. Noordermeer, D. et al. The dynamic architecture of Hox gene clusters. Science 334, 222-5 (2011).
9. Sanyal, A., Lajoie, B. R., Jain, G. & Dekker, J. The long-range interaction landscape of gene promoters. Nature 489, 109-13 (2012).
10. van de Werken, H. J. et al. Robust 4C-seq data analysis to screen for regulatory DNA interactions. Nat Methods 9, 969-72 (2012).
11. de Laat, W. & Duboule, D. Topology of mammalian developmental enhancers and their regulatory landscapes. Nature 502, 499-506 (2013).
12. Hughes, J. R. et al. Analysis of hundreds of cis-regulatory landscapes at high resolution in a single, high-throughput experiment. Nat Genet (2014).
13. Pasquali, L. et al. Pancreatic islet enhancer clusters enriched in type 2 diabetes risk-associated variants. Nat Genet 46, 136-43 (2014).
14. Maurano, M. T. et al. Systematic localization of common disease-associated variation in regulatory DNA. Science 337, 1190-5 (2012).
15. Parker, S. C. et al. Chromatin stretch enhancer states drive cell-specific gene regulation and harbor human disease risk variants. Proc Natl Acad Sci USA 110, 17921-6 (2013).
16. Rao, S. S. et al. A 3D map of the human genome at kilobase resolution reveals principles of chromatin looping. Cell 159, 1665-80 (2014).
17. Jager, R. et al. Capture Hi-C identifies the chromatin interactome of colorectal cancer risk loci. Nat Commun 6, 6178 (2015).
18. Schoenfelder, S. et al. The pluripotent regulatory circuitry connecting promoters to their long-range interacting elements. Genome Res 25, 582-97 (2015).
19. Vernimmen, D., De Gobbi, M., Sloane-Stanley, J. A., Wood, W. G. & Higgs, D. R. Long-range chromosomal interactions regulate the timing of the transition between poised and active gene expression. EMBO J 26, 2041-51 (2007).
20. Hughes, J. R. et al. High-resolution analysis of cis-acting regulatory networks at the alpha-globin locus. Philos Trans R Soc Lond B Biol Sci 368, 20120361 (2013).
21. Bau, D. et al. The three-dimensional folding of the alpha-globin gene domain reveals formation of chromatin globules. Nat Struct Mol Biol 18, 107-14 (2011).
22. Simonis, M. et al. Nuclear organization of active and inactive chromatin domains uncovered by chromosome conformation capture-on-chip (4C). Nat Genet 38, 1348-54 (2006).
23. Kang, J. H. et al. Genomic organization, tissue distribution and deletion mutation of human pyridoxine 5'-phosphate oxidase. Eur J Biochem 271, 2452-61 (2004).

24. Love, M. I., Huber, W. & Anders, S. Moderated estimation of fold change and dispersion for RNA-seq data with DESeq2. Genome Biol 15, 550 (2014).
25. Klein, F. A. et al. FourCSeq: analysis of 4C sequencing data. Bioinformatics (2015).
26. Thongjuea, S., Stadhouders, R., Grosveld, F. G., Soler, E. & Lenhard, B. r3Cseq: an R/Bioconductor package for the discovery of long-range genomic interactions from chromosome conformation capture and next-generation sequencing data. Nucleic Acids Res 41, e132 (2013).
27. Osborne, C. S. et al. Active genes dynamically colocalize to shared sites of ongoing transcription. Nat Genet 36, 1065-71 (2004).
28. Noordermeer, D. et al. Variegated gene expression caused by cell-specific long-range DNA interactions. Nat Cell Biol 13, 944-51 (2011).
29. Bernet, A. et al. Targeted inactivation of the major positive regulatory element (HS-40) of the human alpha-globin gene locus. Blood 86, 1202-11 (1995).
30. Anguita, E. et al. Deletion of the mouse alpha-globin regulatory element (HS-26) has an unexpectedly mild phenotype. Blood 100, 3450-6 (2002).
31. de Wit, E. & de Laat, W. A decade of 3C technologies: insights into nuclear organization. Genes Dev 26, 11-24 (2012).
32. Takahashi, K. & Yamanaka, S. Induction of pluripotent stem cells from mouse embryonic and adult fibroblast cultures by defined factors. Cell 126, 663-76 (2006).
33. Kowalczyk, M. S. et al. Intragenic enhancers act as alternative promoters. Mol Cell 45, 447-58 (2012).
34. Magoc, T. & Salzberg, S. L. FLASH: fast length adjustment of short reads to improve genome assemblies. Bioinformatics 27, 2957-63 (2011).
35. Kent, W. J. et al. The human genome browser at UCSC. Genome Res 12, 996-1006 (2002).
36. Raney, B. J. et al. Track data hubs enable visualization of user-defined genome-wide annotations on the UCSC Genome Browser. Bioinformatics 30, 1003-5 (2014).
37. Buenrostro, et al. (6 Oct. 2013). "Transposition of native chromatin for fast and sensitive epigenomic profiling of open chromatin, DNA-binding proteins and nucleosome position". Nature Methods 10 (12): 1213-1218.

The invention claimed is:

1. A method of identifying nucleic acid regions within a nucleic acid sample which interact with one another, the method comprising the steps:
   A) fragmenting a 3C library which was produced from the nucleic acid sample to produce nucleic acid fragments, wherein the 3C library is or has been produced by the steps of:
      (i) cross-linking a nucleic acid sample;
      (ii) fragmenting the cross-linked nucleic acid sample to produce nucleic acid fragments, wherein the fragmentation step does not or did not comprise the step of labelling the free ends of the nucleic acid fragments with biotin;
      (iii) ligating the nucleic acid fragments to produce ligated nucleic acid fragments; and
      (iv) de-crosslinking the ligated nucleic acid fragments;
   B) adding sequencing adaptors to both ends of the nucleic acid fragments and amplifying the nucleic acid fragments using the sequencing adaptors;
   C) contacting the amplified nucleic acid fragments with a targeting nucleic acid which binds to a subgroup of the amplified nucleic acid fragments, wherein the targeting nucleic acid is labelled with the first half of a binding pair;
   D) isolating the subgroup of nucleic acid fragments which have been bound by the targeting nucleic acid using the second half of the binding pair;
   E) amplifying the isolated subgroup of nucleic acid fragments;
   F) repeating Steps C, D and E; and
   G) sequencing the amplified isolated subgroup of nucleic acid fragments using the sequencing adaptors.

2. The method of claim 1, wherein the targeting nucleic acid is a DNA oligonucleotide.

3. The method of claim 1, wherein concentration of the targeting nucleic acid ranges from 5 µM to 1 pM, 1 µM to 30 pM, 300 nM to 30 pM, or 30 nM to 0.3 nM.

4. The method of claim 1, wherein Step F is repeated 1-5 times or 1 or 2 times.

5. The method of claim 1, wherein the nucleic acid sample is chromatin or DNA.

6. The method of claim 1, wherein the nucleic acid sample is obtained from live cells.

7. The method of claim 1, wherein the nucleic acid sample consists of 1-10,000 cells or 1,000-10,000 cells.

8. The method of claim 1, wherein a restriction endonuclease is used to fragment the cross-linked nucleic acid sample.

9. The method of claim 1, wherein in Step A, the 3C library is fragmented by sonication.

10. The method of claim 1, wherein in Step B, Next Generation sequencing adaptors are added to the ends of the nucleic acid fragments.

11. The method of claim 1, wherein in Step B, the nucleic acid fragments are amplified by PCR.

12. The method of claim 1, wherein in Step C, the targeting nucleic acid is a biotin-labelled DNA.

13. The method of claim 1, wherein in Step D, the second half of the binding pair is a streptavidin-labelled bead.

14. The method of claim 1, wherein in Step E, the isolated subgroup of nucleic acid fragments are amplified using 14-18 PCR cycles.

15. A method of identifying allele-specific interaction profiles in SNP-containing regions, the method comprising the method of claim 1 including sequencing the amplified isolated subgroup of nucleic acid fragments in order to identify allele-specific interaction profiles in SNP-containing regions.

16. A method of identifying one or more interacting nucleic acid regions that are indicative of a particular disease state or disorder, the method comprising:
   a) carrying out a method as claimed in claim 1 on a nucleic acid sample obtained from a subject with a particular disease state or disorder;
   b) quantifying a frequency of interaction between a first nucleic acid region and a second nucleic acid region; and
   c) comparing the frequency of interaction in the nucleic acid sample from the subject with said disease state or disorder with the frequency of interaction in a control nucleic acid sample from a healthy subject, wherein a difference in the frequency of interaction in the nucleic acid samples is indicative of a particular disease state or disorder.

* * * * *